United States Patent
Kim et al.

(10) Patent No.: US 12,421,309 B2
(45) Date of Patent: Sep. 23, 2025

(54) ANTI-TM4SF4 ANTIBODY AND USES THEREOF

(71) Applicant: KOREA ATOMIC ENERGY RESEARCH INSTITUTE, Daejeon (KR)

(72) Inventors: In Gyu Kim, Daejeon (KR); Rae Kwon Kim, Sejong (KR); Jai Ha Lee, Daejeon (KR); Chang Kyu Heo, Daejeon (KR); Yeon Jee Kahm, Hwaseong-si (KR); Byung Chul Shin, Seoul (KR); Eun Wie Cho, Daejeon (KR); Chun Jeih Ryu, Seoul (KR); Min Kyu Kim, Seoul (KR); Mun Ju Choi, Seoul (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 835 days.

(21) Appl. No.: 17/299,156

(22) PCT Filed: Dec. 4, 2020

(86) PCT No.: PCT/KR2020/017699
§ 371 (c)(1),
(2) Date: Jun. 2, 2021

(87) PCT Pub. No.: WO2021/112640
PCT Pub. Date: Jun. 10, 2021

(65) Prior Publication Data
US 2023/0002485 A1 Jan. 5, 2023

(30) Foreign Application Priority Data
Dec. 6, 2019 (KR) .................. 10-2019-0162068

(51) Int. Cl.
| C07K 16/28 | (2006.01) |
| A61K 39/00 | (2006.01) |
| A61P 11/00 | (2006.01) |
| A61P 35/00 | (2006.01) |

(52) U.S. Cl.
CPC .............. *C07K 16/28* (2013.01); *A61P 11/00* (2018.01); *A61P 35/00* (2018.01); *A61K 2039/505* (2013.01); *C07K 2317/21* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 7,785,801 | B2 | 8/2010 | Türeci et al. |
| 8,445,722 | B2 | 5/2013 | Park et al. |
| 8,778,901 | B2 | 7/2014 | Park et al. |
| 9,072,698 | B2 | 7/2015 | Park et al. |
| 9,075,064 | B2 | 7/2015 | Kim et al. |
| 9,255,131 | B2 | 2/2016 | Türeci et al. |
| 9,334,331 | B2 * | 5/2016 | Igawa .................... C07K 16/36 |
| 9,533,043 | B2 | 1/2017 | Türeci et al. |
| 10,059,773 | B2 | 8/2018 | Zhang et al. |
| 10,421,807 | B2 * | 9/2019 | Gonzales ............. C07K 16/244 |
| 10,724,103 | B2 | 7/2020 | Türeci et al. |
| 2002/0115057 | A1 | 8/2002 | Young |
| 2008/0193454 | A1 | 8/2008 | Tureci et al. |
| 2009/0130102 | A1 | 5/2009 | Weaver et al. |
| 2010/0068730 | A1 | 3/2010 | Park et al. |
| 2010/0081638 | A1 | 4/2010 | Lee et al. |
| 2011/0014628 | A1 | 1/2011 | Türeci et al. |
| 2011/0177098 | A1 | 7/2011 | Sussel et al. |
| 2011/0318361 | A1 | 12/2011 | Park et al. |
| 2012/0282619 | A1 | 11/2012 | Park et al. |
| 2014/0120085 | A1 | 5/2014 | Türeci et al. |
| 2014/0234326 | A1 | 8/2014 | Kim et al. |
| 2016/0193335 | A1 | 7/2016 | Tureci et al. |
| 2016/0362498 | A1 | 12/2016 | Zhang et al. |
| 2017/0073395 | A1 | 3/2017 | Finlay et al. |
| 2018/0169236 | A1 | 6/2018 | Tureci et al. |
| 2018/0346585 | A1 | 12/2018 | Zhang et al. |
| 2019/0231872 | A1 | 8/2019 | Kwon et al. |

FOREIGN PATENT DOCUMENTS

| CN | 101748122 A | 6/2010 |
| EP | 1498424 A2 | 1/2005 |
| JP | 2007-537197 A | 12/2007 |
| JP | 2008-283945 A | 11/2008 |
| JP | 2009-530422 A | 8/2009 |

(Continued)

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
International Search Report dated Mar. 11, 2021 for corresponding International Patent Application No. PCT/KR2020/017699.

(Continued)

*Primary Examiner* — Elizabeth C. Kemmerer
(74) *Attorney, Agent, or Firm* — Hauptman Ham, LLP

(57) ABSTRACT

The present invention relates to novel antibodies or antigen-binding fragments thereof that specifically bind to Trans-Membrane 4 Superfamily Member 4 (TM4SF4). These antibodies or antigen-binding fragments thereof exhibit proliferation inhibitory activity of cancer cells so as to effectively prevent or treat cancer, and reduce the self-renewal ability of cancer stem cells to be usefully used even in the treatments of cancer with a poor prognosis in conventional anticancer treatments.

17 Claims, 18 Drawing Sheets

Specification includes a Sequence Listing.

(56) References Cited

FOREIGN PATENT DOCUMENTS

| JP | 2014-528944 A | 10/2014 |
|---|---|---|
| KR | 10-2008-0052391 A | 6/2008 |
| KR | 10-2008-0058022 A | 6/2008 |
| KR | 10-0906145 B1 | 7/2009 |
| KR | 10-2013-0033075 A | 4/2013 |
| KR | 10-1314828 B1 | 10/2013 |
| KR | 10-1836392 B1 | 3/2018 |
| KR | 10-2021-0071856 A | 6/2021 |
| WO | 2004/073657 A2 | 9/2004 |
| WO | 2013/047941 A1 | 4/2013 |
| WO | 2021/112640 A1 | 6/2021 |

OTHER PUBLICATIONS

Written Opinion dated Mar. 11, 2021 for corresponding International Patent Application No. PCT/KR2020/017699.
Soo-Im Choi et al., "TM4SF4 overexpression in radiation-resistant lung carcinoma cells activates IGF1R via elevation of IGF1," Oncotarget, Sep. 8, 2014, pp. 9823-9837, vol. 5, No. 20, cited in NPL Nos. 1 and 2, and the Specification.
GenBank Accession No. AAP36961.1, "*Homo sapiens* transmembrane 4 superfamily member 4, partial [synthetic construct]," Jul. 25, 2016, cited in NPL Nos. 1 and 2.
Soo-Im Choi et al., "Osteopontin production by TM4SF4 signaling drives a positive feedback autocrine loop with the STAT3 pathway to maintain cancer stem cell-like properties in lung cancer cells," Oncotarget, Sep. 18, 2017, pp. 101284-101297, vol. 8, No. 60, cited in NPL Nos. 1 and 2.
Charles Yanofsky et al., "Repression is Relieved I3efore Attenuation in the trp Operon of *Escherichia coli* as Tryptophan Starvation Becomes Increasingly Severe," Journal of Bacteriology, Jun. 1984, pp. 1018-1024, vol. 158, No. 3, cited in the Specification.
Ira Herskowitz et al., "The Lysis-Lysogeny Decision of Phage Lambda: Explicit Programming and Reponsiveness," Ann. Rev. Genet, 1980, pp. 399-445, vol. 14, cited in the Specification.
Hyun-Woo Park et al., "Optimization of Cry3A Yields in Bacillus thuringiensis by use of Sporulation-Dependent Promoters in Combination with the STAB-SD mRNA Sequence," Applied and Environmental Microbiology, Oct. 1998, pp. 3932-3938, vol. 64, No. 10, cited in the Specification.
Alejandra Bravo et al., "Analysis of crylAa expression in sigE and sigK mutants of Bacillus thuringiensis," Mol Gen Genet, 1996, pp. 734-741, vol. 250, cited in the Specification.
Zhongde Wang et al., "Universal PCR amplification of mouse immunoglobulin gene variable regions: the design of degenerate primers and an assessment of the effect of DNA polymerase 3X to 5X exonuclease activity," Journal of Immunological Methods, 2000, pp. 167-177, vol. 233, cited in the Specification.
Ying Li et al., "Human tetraspanin transmembrane 4 superfamily member 4 or intestinal and liver tetraspan membrane protein is overexpressed in hepatocellular carcinoma and accelerates tumor cell growth," Acta Biochim Biophys Sin, 2012, pp. 224-232, vol. 44, Issue 3.
W. Franklin et al., "Detection of RNA biomarkers in sputum of lung cancer patients and high risk smokers," 11th world conference on Lung cancer, Jul. 3-6, 2005, Barcelona, Spain, abstract p. 245.
Dandrea et al., "The Transcriptosomal Response of Human A549 Lung Cells to a Hydrogen Peroxide-Generating System: Relationship to DNA Damage, Cell Cycle Arrest, and Caspase Activation," Free Radical Biology & Medicine, vol. 36, No. 7, 2004, pp. 881-896.
Nakamura et al., "Identification of tumor markers and differentiation markers for molecular diagnosis of lung adenocarcinoma," Oncogene, Feb. 20, 2006, vol. 25, pp. 4245-4255.
Qiu et al., "Overexpression of the gene for transmembrane 4 superfamily member 4 accelerates liver damage in rats treated with CCI4," Journal of Hepatology, Oct. 2, 2006, vol. 46, pp. 266-275; cited in NPL Nos. 15 & 16.
Juan Angel Fresno Vara et al., "PI3K/Akt signalling pathway and cancer," Cancer Treatment Reviews, Apr. 2004, vol. 30, No. 2, pp. 193-204.
Rundhaug, "Matrix Metalloproteinases, Angiogenesis, and Cancer," Clinical Cancer Research, Feb. 2003, vol. 9, No. 2, pp. 551-554.
Wright et al., "The L6 membrane proteins—A new four-transmembrane superfamily," Protein Science, 2000, vol. 9, No. 8, pp. 1594-1600.
Zevian et al., "Structure-Function Analysis of Tetraspanin CD151 Reveals Distinct Requirements for Tumor Cell ~," The Journal of Biological Chemistry, Dec. 2, 2010, vol. 286, No. 9, pp. 7496-7506.
Lee et al., "Tetraspanin TM4SF5 mediates loss of contact inhibition through epithelial-mesenchymal transition in human hepatocarcinoma," The Journal of Clinical Investigation, Apr. 2008, vol. 118, No. 4, pp. 1354-1366.
Choi et al., "Cooperation between integrin alpha 5 and tetraspan TM4SF5 regulates VEGF-mediated angiogenic activity," Blood, Nov. 25, 2008, vol. 113, No. 8, pp. 1845-1855.
Lui et al., "Molecular cloning of a cDNA for rat TM4SF4, a homolog of human il-TMP(TM4SF4), and enhanced expression of the corresponding gene in regenerating rat liver," Biochimica et Biophysica Acta, 2001, vol. 1518, pp. 183-189.
Anderson et al., "The L6 domain tetraspanin Tm4sf4 regulates endocrine pancreas differentiation and directed cell migration," Development, 2011, vol. 138, No. 15, pp. 3213-3224.
Japanese Office Action issued on Jun. 28, 2022, in connection with the Japanese Patent Application No. 2021-542571, 7 pages, along with English machine translation.
International Search Report issued Sep. 20, 2022, corresponding to International Patent Application No. PCT/KR2022/008570, 4 pages.
Written Opinion issued Oct. 12, 2012, corresponding to International Patent Application No. PCT/KR2011/007900, 10 pages, along with English machine translation.
International Search Report issued Oct. 12, 2012, corresponding to International Patent Application No. PCT/KR2011/007900, 8 pages, along with English machine translation.
Written Opinion issued Mar. 11, 2021, corresponding to International Patent Application No. PCT/KR2020/017699, 6 pages, along with English machine translation.
International Search Report issued Mar. 11, 2021, corresponding to International Patent Application No. PCT/KR2020/017699, 8 pages, along with English machine translation.
Jung, Kyungsoo et al., "TM4SF4 and LRRK2 are Potential Therapeutic Targets in Lung and Breast Cancers through Outlier Analysis", Cancer Res Treat, 2021, vol. 53, Issue 1, pp. 9-24.
The Extended European Search Report dated Nov. 18, 2024 for corresponding European Patent Application No. 22825362.1 (8 pages).
Office Action dated Jan. 7, 2025 for corresponding Japanese Patent Application No. 2023-578042, along with an English translation (12 pages).
Yoonjoo Choi et al., "Antibody humanization by structure-based computational protein design", mAbs, vol. 7, No. 6, Aug. 7, 2015, pp. 1045-1057, cited in NPL No. 1.
Johnathan D. Guest et al., "An Expanded Benchmark for Antibody-Antegen Docking and Affinity Prediction Reveals Insights into Antibody Recognition Determinants", Structure, vol. 29, No. 6, Jun. 3, 2021 (39 pages), cited in NPL No. 1.
Toshio Akimoto, "Human Reshaped Antibodies", Journal of the Crystallographic Society of Japan, vol. 37, 1995, pp. 134-136, cited in NPL No. 2, with English abstract.
Kouhei Tsumoto, "Dissection of antibody-antigen interactions for development of antibodies", Drug Delivery System, vol. 28, Issue 5, 2013, pp. 412-423, cited in NPL No. 2, with English abstract.

* cited by examiner

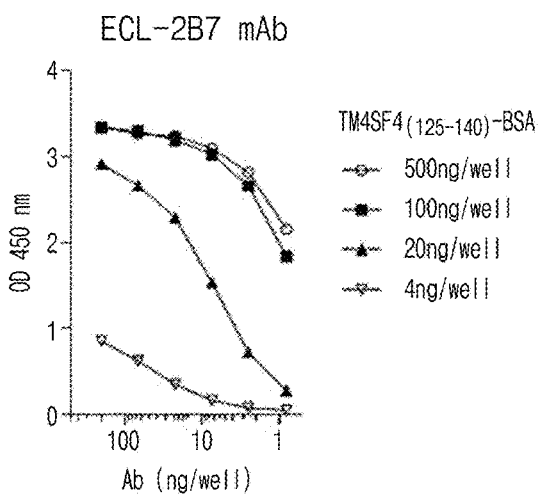
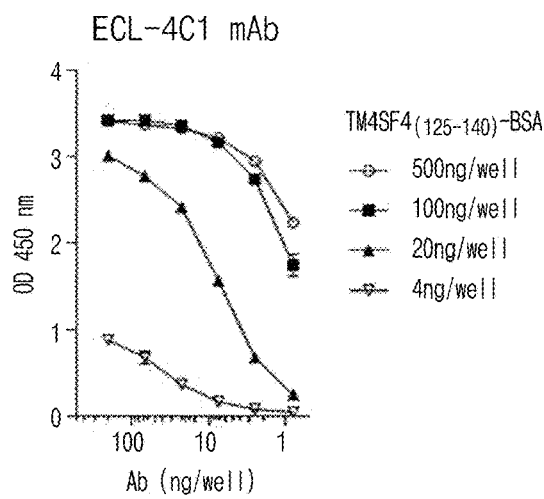
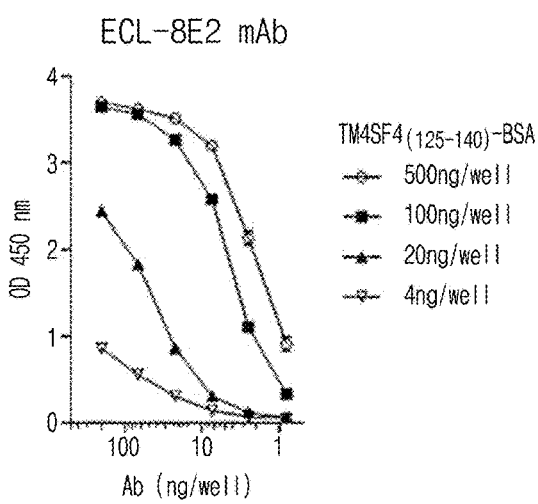
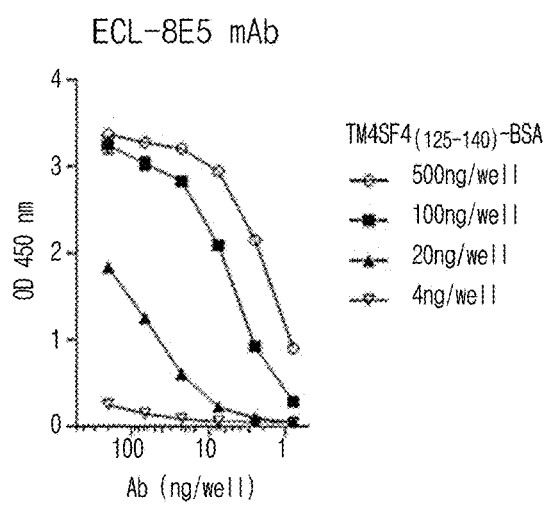
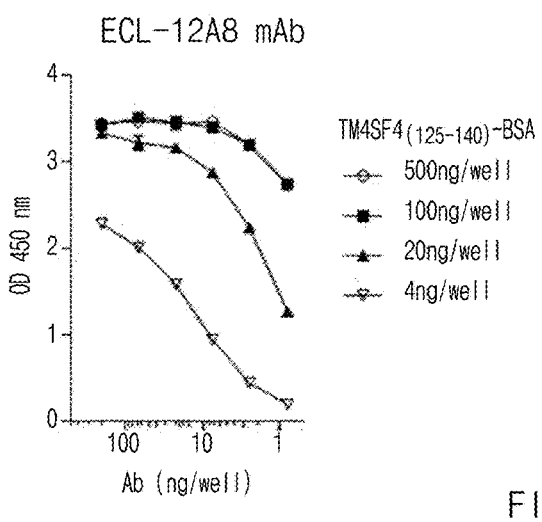
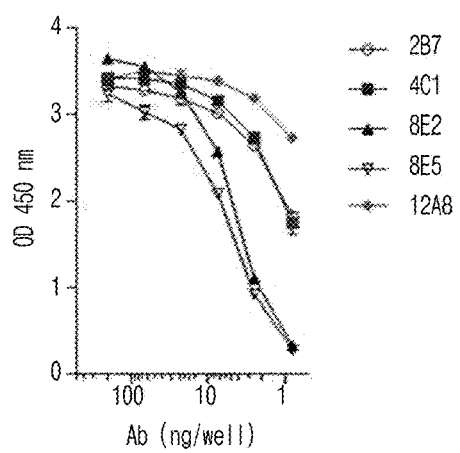
FIG. 3

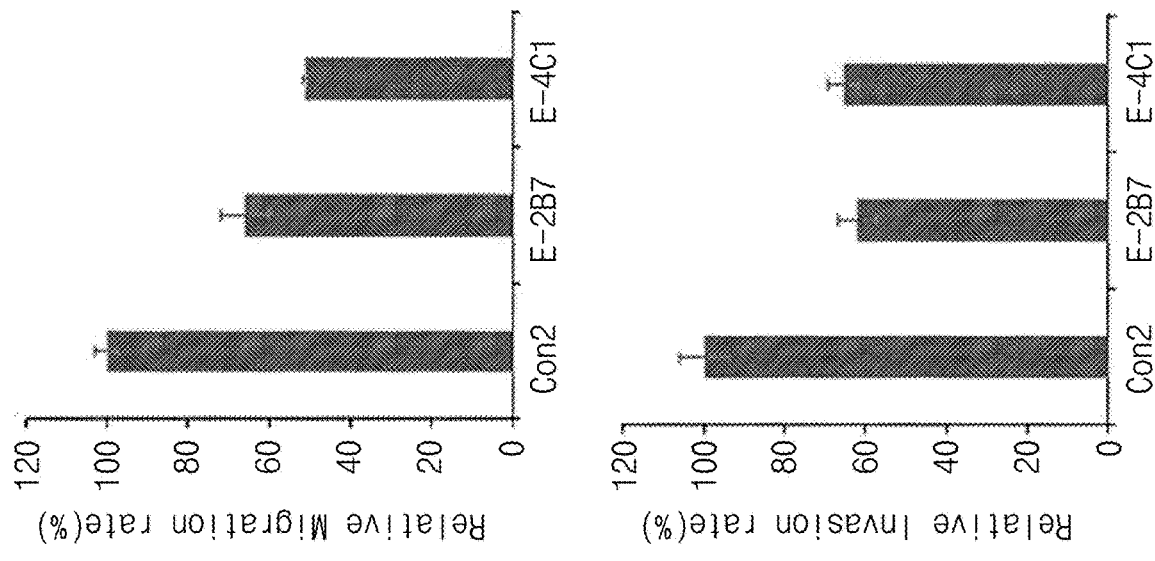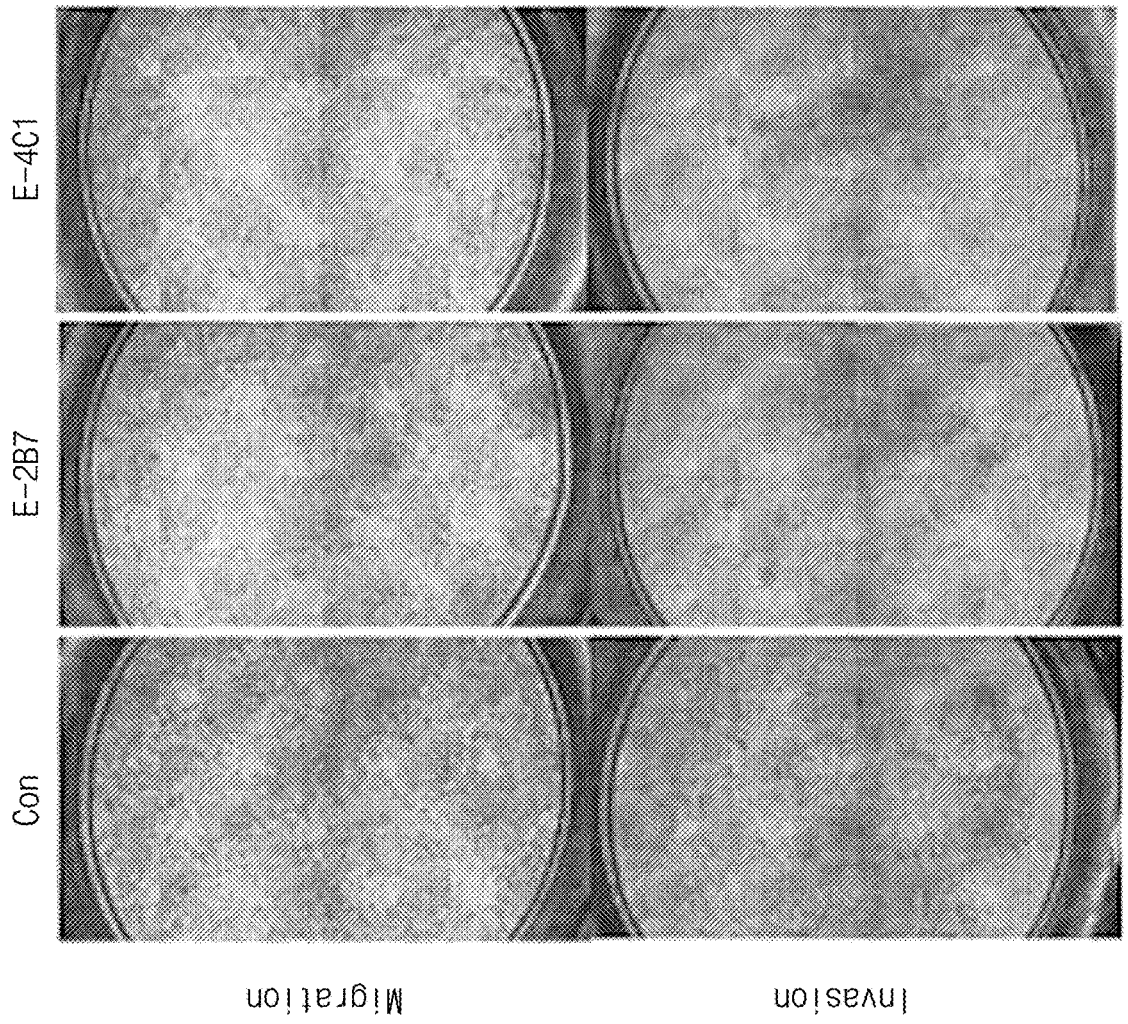
FIG. 8

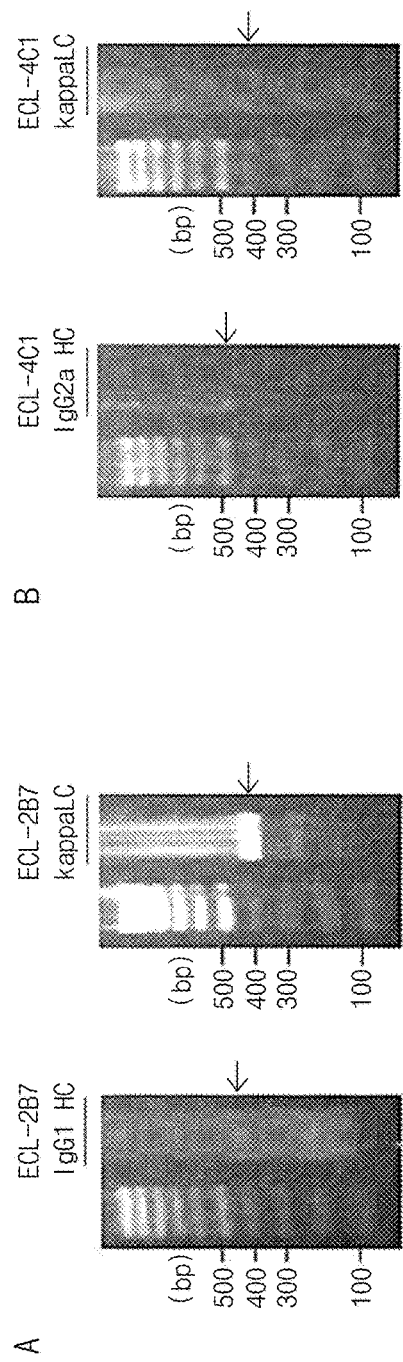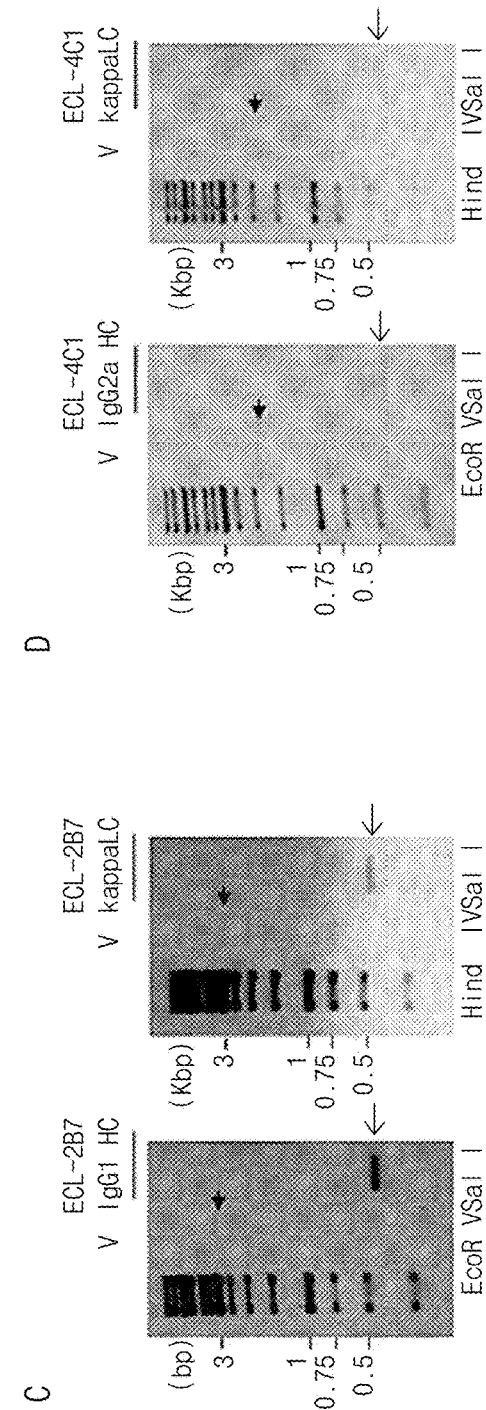
FIG. 12

<ECL-287 Heavy chain variable region : Subgroup (IIIC)

| | | | | | | | | | | | | | |
|---|---|---|---|---|---|---|---|---|---|---|---|---|---|
| Sequence ID No. 17 | GAG | GTG | AAG | CTG | GAG | GAG | TCT | GGC | CCT | GGG | ATA | TTG | CAG | CCC | 42 |
| Sequence ID No. 15 | Glu | Val | Lys | Leu | Glu | Glu | Ser | Gly | Pro | Gly | Ile | Leu | Gln | Pro | 14 |

```
              TCC CAG ACC CTC AGT CTG ACT TGT TCT TTC TCT GGG TTT TCA    84
              Ser Gln Thr Leu Ser Leu Thr Cys Ser Phe Ser Gly Phe Ser    28
                      31 CDR-H1
              CTG AGC ACT TAT GGT ATA GGC GTA AGC TGG ATT CGT CAG CCT   126
              Leu Ser Thr Tyr Gly Ile Gly Val Ser Trp Ile Arg Gln Pro    42
                                                52 CDR-H2
              TCT GGG AAG GGT CTG GAG TGG CTG GCA CAC ATT TGG TGG AAT   210
              Ser Gly Lys Gly Leu Glu Trp Leu Ala His Ile Trp Trp Asn    56

GAT AAT AAG TAC TAT AAC ACA GCC CTG AAG AGC CGG CTC ACA   210
              Asp Asn Lys Tyr Tyr Asn Thr Ala Leu Lys Ser Arg Leu Thr    70

ATC TCC AAG GAT ACC TCC AAC AAC CAG GTA TTC CTC AAG ATC   252
              Ile Ser Lys Asp Thr Ser Asn Asn Gln Val Phe Leu Lys Ile    84

GCC AGT GTG GAC ACT GCA GAT ACT GCC ACA TAC TAC TGT GCT   294
              Ala Ser Val Asp Thr Ala Asp Thr Ala Thr Tyr Tyr Cys Ala    98
                      100 CDR-H3
              CGA AAG GAG GGC AGC TCG GCC CCC TTT GCT TAC TGG GGC CAA   336
              Arg Lys Glu Gly Ser Ser Ala Pro Phe Ala Tyr Trp Gly Gln   112

GGG ACT CTG GTC ACT GTC TCT GCA                          360
              Gly Thr Leu Val Thr Val Ser Ala                          120
```

FIG. 13A

<ECL-2B7 kappa chain variable region : Subgroup (V)>

| | | |
|---|---|---|
| Sequence ID No. 18 | GAT ATT GTG ATG ACC CAG TCT CCA TCC TCC CTG GCT ATG TCA | 42 |
| Sequence ID No. 16 | Asp Ile Val Met Thr Gln Ser Pro Ser Ser Leu Ala Met Ser | 14 |

24 CDR-L1

```
GTA GGA CAG AAG GTC ACT ATG AGC TGC AAG TCC AGT CAG AGC    84
Val Gly Gln Lys Val Thr Met Ser Cys Lys Ser Ser Gln Ser   28

CTT TTA AAT AGT AGC AAT CAA AAG AAC TAT TTG GCC TGG TAC   126
Leu Leu Asn Ser Ser Asn Gln Lys Asn Tyr Leu Ala Trp Tyr    42
                                                           56
CAG CAG AAA CCA GGA CAG TCT CCT AAA CTT CTG ATA TAC TTT   168
Gln Gln Lys Pro Gly Gln Ser Pro Lys Leu Leu Ile Thr Phe    56
CDR-L2
GCA TCC ACT AGG GAA TCT GGG GTC CCT GAT CGC TTC ATA GGC   210
Ala Ser Thr Arg Glu Ser Gly Val Pro Asp Arg Phe Ile Gly    70

AGT GGA TCT GGG ACA GAT TTC ACT CTT ACC ATC AGC AGT ATG   252
Ser Gly Ser Gly Thr Asp Phe Thr Leu Thr Ile Ser Ser Met    84
                                                  96 CDR-L3
CAG GCT GAA GAC CTG GCA GAT TAC TTC TGT CAG CAA CAT TAT   294
Gln Ala Glu Asp Leu Ala Asp Tyr Phe Cys Gln Gln His Tyr    98

AGA ACT CCT CCG ACG TTC GGT GGA GGC ACC AAG CTG GAA ATC   336
Arg Thr Pro Pro Thr Phe Gly Gly Gly Thr Lys Leu Glu Ile   112

AAA CGG                                                   342
Lys Arg                                                   114
```

FIG. 13B

```
<CCL-2B7 Heavy chain variable region : Subgroup (IIIC)

Sequence ID No. 21   GAA GTT AAG CTG GAG GAG TCT GGC CCT GGG ATA TTG CAG CCC    42
Sequence ID No. 19   Glu Val Lys Leu Glu Glu Ser Gly Pro Gly Ile Leu Gln Pro    14

TCC CAG ACC CTC AGT CTG ACT TGT TCT TTC TCT GGG TTT TCA    84
                     Ser Gln Thr Leu Ser Leu Thr Cys Ser Phe Ser Gly Phe Ser    28
                              31 CDR-H1
                     CTG AGC ACT TAT GGT ATA GGA GTA AGC TGG ATT CGT CAG CCT   126
                     Leu Ser Thr Tyr Gly Ile Gly Val Ser Trp Ile Arg Gln Pro    42
                                                          52 CDR-H2
                     TCT GGG AAG GGT CTG GAG TGG CTG GCA CAC ATT TGG TGG AAT   210
                     Ser Gly Lys Gly Leu Glu Trp Leu Ala His Ile Trp Trp Asn    56

GAT AAT AAG TAC TAT AAC ACA GCC CTG AAG AGC CGG CTC ACA   210
                     Asp Asn Lys Tyr Tyr Asn Thr Ala Leu Lys Ser Arg Leu Thr    70

ATC TCC AAG GAT ACG TCC AAC AAC CAG GTA TTC CTC AAG ATC   252
                     Ile Ser Lys Asp Thr Ser Asn Asn Gln Val Phe Leu Lys Ile    84

GCC AGT GTG GAC ACT GCA GAT ACT GCC ACA TAC TAC TGT GCT   294
                     Ala Ser Val Asp Thr Ala Asp Thr Ala Thr Tyr Tyr Cys Ala    98
                              100 CDR-H3
                     CGA AAG GAG GGC AGC TGG GCC CCC TTT GCT TTC TGG GGC CAA   336
                     Arg Lys Glu Gly Thr Ser Ala Pro Phe Ala Phe Trp Gly Gln   112

GGG ACT CTG GTC CAT GTC TCT GCA                           360
                     Gly Thr Leu Val Thr Val Ser Ala                           120
```

FIG. 14A

<ECL-4C1 kappa chain variable region : Subgroup (V)>

| | | |
|---|---|---|
| Sequence ID No. 22 | GAT ATT GTG ATG ACC CAG TCT CCA TCC TCC CTG GCT ATG TCA | 42 |
| Sequence ID No. 20 | Asp Ile Val Met Thr Gln Ser Pro Ser Ser Leu Ala Met Ser | 14 |

24 CDR-L1

GTA GGA CAG AAG GTC ACT ATG AGC TGC <u>AAG TCC AGT CAG AGC</u> 84
Val Gly Gln Arg Val Thr Met Ser Cys <u>Lys Ser Ser Gln Ser</u> 28

<u>CTT TTA AAT GGT AGC AAT CAA AAG AAC TAT TTG GCC</u> TGG TTC 126
<u>Leu Leu Asn Gly Ser Asn Gln Lys Asn Tyr Leu Ala</u> Trp Phe 42

56
CAG CAG AAA CCA GGA CAG TCT CCT AAA CTT CTG GTA TAC <u>TTT</u> 168
Gln Gln Lys Pro Gly Gln Ser Pro Lys Leu Leu Val Tyr <u>Phe</u> 56
<u>CDR-L2</u>
<u>GCA TCC ACT AGG GAA TCT</u> GGG GTC CCT GAT CGC TTC ATA GGC 210
<u>Ala Ser Thr Arg Glu Ser</u> Gly Val Pro Asp Arg Phe Ile Gly 70

AGT GGA TCT GGG ACA GAT TTC ACT CTT ACC ATC AGC AGT GTG 252
Ser Gly Ser Gly Thr Asp Phe Thr Leu Thr Ile Ser Ser Val 84

95 CDR-L3
CAG GCT GAA GAC CTG GCA GAT TAC TTC TGT <u>CAG CAA CAT TAT</u> 294
Gln Ala Glu Asp Leu Ala Asp Tyr Phe Cys <u>Gln Gln His Tyr</u> 98

<u>AGA ACT CCT CCG ACG</u> TTC GGT GGA GGC ACC AAG CTG GAA ATC 336
<u>Arg Thr Pro Pro Thr</u> Phe Gly Gly Gly Thr Lys Leu Glu Ile 112

AAA CGG 342
Lys Arg 114

FIG. 14B

ANTI-TM4SF4 ANTIBODY AND USES THEREOF

CROSS-REFERENCE TO RELATED APPLICATION

The present application is a national stage filing under 35 U.S.C. § 371 of PCT application number PCT/KR2020/017699 filed on Dec. 4, 2020 which is based upon and claims the benefit of priorities to Korean Patent Application No. 10-2019-0162068, filed on Dec. 6, 2019, in the Korean Intellectual Property Office, which is incorporated herein in its entirety by reference.

INCORPORATION BY REFERENCE

The sequence listing of the present application is submitted electronically via EFS-Web as an ASCII formatted sequence listing with a file name "F-04-5900-0030_Sequence_Listing_Amended_CRF2.txt", with a creation date of May 12, 2025, and a size of 15,830 bytes. This sequence_listing submitted via EFS-Web is part of the specification and is herein incorporated by reference in its entirety.

TECHNICAL FIELD

The present invention relates to an antibody or antigen-binding fragment thereof that specifically binds to TransMembrane 4 Superfamily Member 4 (TM4SF4), and a composition for preventing or treating cancer comprising the same.

BACKGROUND ART

It has been reported that TransMembrane 4 Superfamily Member 4 (TM4SF4) is a type of tetraspanin protein, and other proteins of this class, TM4SF1 and TM4SF5, are up-regulated in expression in many tumors and are involved in epithelial-mesenchymal metastasis and cell migration, and a number of studies associated with cancer cells have been conducted. It has been reported that TM4SF4 is involved in apoptosis and differentiation and invasion capacity of cells in cancer cells. However, there is nothing known about the characteristics of cancer stem cells, and no studies thereof have been conducted. Recently, researchers of the present invention have reported that the TM4SF4 protein promotes cancer stem cell growth, self-renewal ability, and metastasis/invasion in human lung cancer cells. In addition, the researchers have suggested that TM4SF4 promotes the activation of IGF1Rβ/AKT/NFκB or JAK2 (or FAK)/STAT3 as an important signaling system in cancer occurrence, and enhances the characteristics of cancer stem cells by secretion of cytokines that are promoted thereby to make tumors more malignant (Choi S I et al., Oncotarget. 2014; 5 (20): 9823-9837, Choi S I et al., Oncotarget. 2017; 8 (60): 101284-101297).

Antibodies have been used as therapeutic agents due to high binding specificity to target antigens and stability in the human body. In particular, antibodies with anti-cancer functions are improved to humanized antibodies, single-chain antibodies, double antibodies, and drug-fusion antibodies based on the development of antibody engineering technology to greatly improve the cancer treatment efficacy and have been utilized. However, due to the diversity of cancer characteristics and the induction of resistance to treatment by expression of new antigens, limitations are being pointed out in the types of antigens that are used for targeting cancer cells in the related art, and research continues to search for novel cancer-specific antigens and to derive antibodies against the antigens.

In particular, in the case of cancer that shows resistance to target drugs or radiation therapy which have been used in existing cancer treatments and recurs, it has been reported that the characteristics of cancer stem cells are importantly applied, and as a result, discovery of antigens and securing of specific antibodies that may be used for targeting cancer stem cells are being magnified in importance.

Under this technical background, the present inventors have made many efforts to develop novel antibodies targeting cancer stem cells, and as a result, developed novel anti-TM4SF4 antibodies that binds to TM4SF4 with high affinity, and found that the novel antibodies not only significantly inhibited the proliferation of tumor cells including cancer stem cells, but also had excellent anticancer effects, and then completed the present invention.

DISCLOSURE

Technical Problem

Accordingly, an object of the present invention is to provide an antibody or antigen-binding fragment thereof that specifically binds to TransMembrane 4 Superfamily Member 4 (TM4SF4).

Another object of the present invention is to provide a nucleic acid molecule coding the antibody or antigen-binding fragment thereof, an expression vector comprising the nucleic acid molecule, a host cell comprising the expression vector, and a method for producing an antibody or antigen-binding fragment thereof comprising culturing the host cell.

Yet another object of the present invention is to provide a composition for detecting TM4SF4 comprising the antibody or antigen-binding fragment thereof, a detection kit comprising the same, and a method for detecting a TM4SF4 antigen using the same.

Still another object of the present invention is to provide a pharmaceutical composition for preventing or treating cancer comprising the antibody or antigen-binding fragment thereof; a composition for inhibiting growth of cancer stem cells; and a composition for adjuvant chemoradiation therapy.

Technical Solution

In order to achieve the objects, an aspect of the present invention provides an antibody or antigen-binding fragment thereof that specifically binds to TransMembrane 4 Superfamily Member 4 (TM4SF4).

Another aspect of the present invention provides a nucleic acid molecule coding the antibody or antigen-binding fragment thereof.

Yet another aspect of the present invention provides an expression vector comprising the nucleic acid molecule.

Still another aspect of the present invention provides a host cell comprising the expression vector.

Still another aspect of the present invention provides a method for producing an antibody or antigen-binding fragment thereof comprising culturing the host cell.

Still another aspect of the present invention provides a composition and a kit for detecting TM4SF4 comprising the antibody or antigen-binding fragment thereof.

Still another aspect the present invention provides a method for detecting a TM4SF4 antigen comprising contacting the antibody or antigen-binding fragment thereof with a sample to be detected which is expected to include the TM4SF4 antigen.

Still another aspect of the present invention provides a pharmaceutical composition for preventing or treating cancer comprising (a) a therapeutically effective dose of the antibody or antigen-binding fragment thereof; and (b) a pharmaceutically acceptable carrier.

Still another aspect of the present invention provides a composition for inhibiting growth of cancer stem cells.

Still yet another aspect of the present invention provides a composition for adjuvant chemoradiation therapy comprising an antibody or antigen-binding fragment thereof.

Advantageous Effects

The antibody or antigen-binding fragment thereof that specifically binds to TM4SF4 of the present invention has a novel sequence and exhibits excellent cancer cell proliferation inhibitory activity, thereby effectively preventing or treating diseases such as cancer.

In addition, the growth of cancer stem cells may be inhibited by reducing the self-renewal ability, invasion ability, and migration ability of cancer stem cells, thereby effectively treating cancer resistant to existing anticancer treatment methods.

In addition, existing anticancer agents or radiation therapy are treated in combination to further increase the anticancer activity, the usage of anticancer agents may be drastically reduced to reduce side effects caused by the use of anticancer agents, and as a technology capable of remarkably improving the effect of chemoradiation therapy for a subject who is not easily treated due to resistance to conventional radiation therapy, it is useful for the treatment of cancer with a poor prognosis of conventional anticancer treatments.

Therefore, the novel antibodies or antigen-binding fragments thereof of the present invention can be usefully used in the development of novel antibody drugs targeting TM4SF4.

DESCRIPTION OF DRAWINGS

FIG. 3 illustrates an antigen responsivity by novel antibodies of the present invention by performing ELISA against a TM4SF4 (126-140)-BSA antigen. The antigen was coated at a level of 500 to 4 ng/well, and the antibody was treated in a range (200 to 0.8 ng/well) indicated on an X-axis. All the five antibodies showed a high responsivity to a peptide antigen (A to E). In particular, when comparing the results by ELISA using 100 ng/well of a peptide-coated antigen, it can be seen that antibodies 2B7, 4Cl, and 12A8 show high antigen affinity (F).

FIG. 6A illustrates a result of verifying that the novel antibody binds to EGFP-TM4SF4 expressed on a HEK293T cell surface, and FIG. 6B result of illustrates a verifying 41 that the novel antibody specifically binds to TM4SF4 existing on the surface of A549 cells. In particular, when siRNA inhibits the expression of a TM4SF4 antigen, it was confirmed that the antibody response disappeared, and it was again verified that the novel antibody specifically binds to the TM4SF4 antigen.

FIG. 8 illustrates confirming an effect of inhibiting migration ability and invasion ability of cancer cells by the novel antibodies of the present invention. ECL-2B7 and ECL-4C1 were used as the novel antibodies, and an anti-TM4SF4 antibody of Sigma was used as a control (con). The left side is to observe migrated cells and invaded cells by staining, and the right side is a graph showing relative migration ability and invasion ability with respect to the control. In a migration experiment, three repeat experiments were performed for a total of 4 times, and in an invasion experiment, three repeat experiments were performed 3 times.

FIG. 12 illustrates results of performing RT-PCR and cloning for sequencing of complementarity determining regions (CDRs) of the novel antibodies of the present invention: An IgG1 subtype heavy chain gene and a kappa light chain gene (A) of an ECL-2B7 antibody, and an IgG2a subtype heavy chain gene and a kappa light chain gene (B) of an ECL-4C1 antibody were amplified by RT-PCR using primers containing restriction enzyme sequences and cloned into a vector. The sequences cloned into the vector were again confirmed by cleavage of the restriction enzymes, and then nucleotide sequencing on the antibody gene site was performed. The heavy chain gene of each antibody was cleaved with EcoRI and SalI, and the light chain gene was cleaved with HindIII and SalI to be identified on an agarose gel. Black arrow: Vector (V) after cleavage, Arrow: Cleaved insert genes (C, D).

FIG. 13A illustrates results of analyzing a nucleotide sequence and a protein sequence of a heavy chain variable region of a novel antibody ECL-2B7. The antigen recognition determining regions according to the antibody structure were arranged through Kabat numbering and indicated in the sequence as CDRs 1, 2, and 3.

FIG. 13B illustrates of results 41 analyzing a nucleotide sequence and a protein sequence of a light chain variable region of the novel antibody ECL-2B7. The antigen recognition determining regions according to the antibody structure were arranged through Kabat numbering and indicated in the sequence as CDRs 1, 2, and 3.

FIG. 14A illustrates results of analyzing a nucleotide sequence and a protein sequence of a heavy chain variable region of a novel antibody ECL-4C1. The antigen recognition determining regions according to the antibody structure were arranged through Kabat numbering and indicated in the sequence as CDRs 1, 2, and 3.

FIG. 14B illustrates results of analyzing a nucleotide sequence and a protein sequence of a light chain variable region of the novel antibody ECL-4C1. The antigen recognition determining regions according to the antibody structure were arranged through Kabat numbering and indicated in the sequence as CDRs 1, 2, and 3.

BEST MODE

Figure 1:
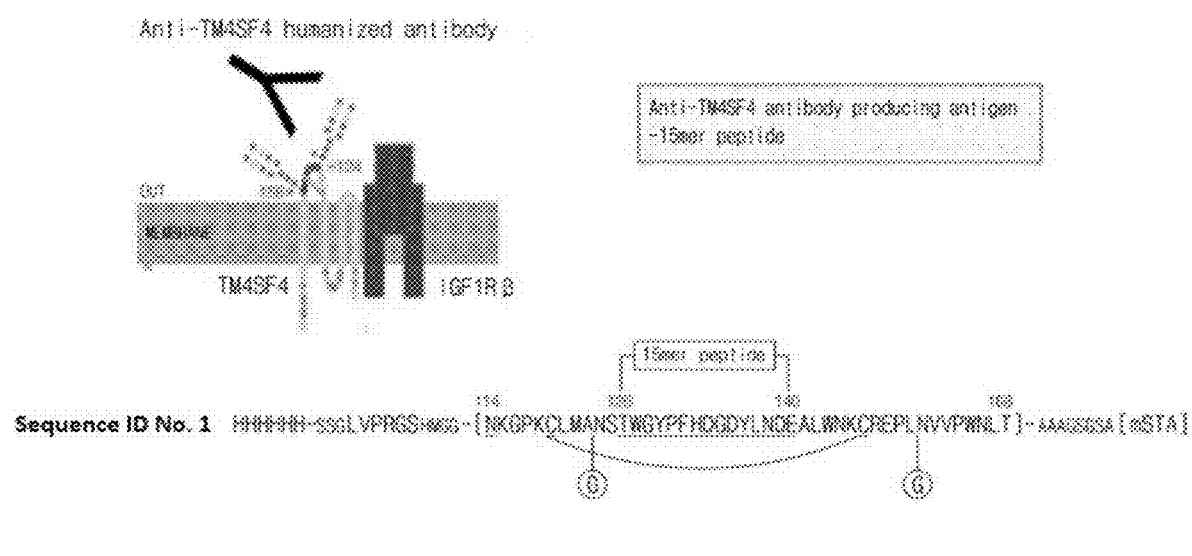
FIG. 1 illustrates an epitope region in a TM4SF4 protein to which an antibody or antigen-binding fragment thereof of the present invention specifically binds: The epitope region represents a 15mer peptide at positions 126 to 140 of a region exposed outside a cell membrane of the TM4SF4 protein; G represents a glycosylation site; and C represents cysteine that forms a disulfide bond.
Figure 2:
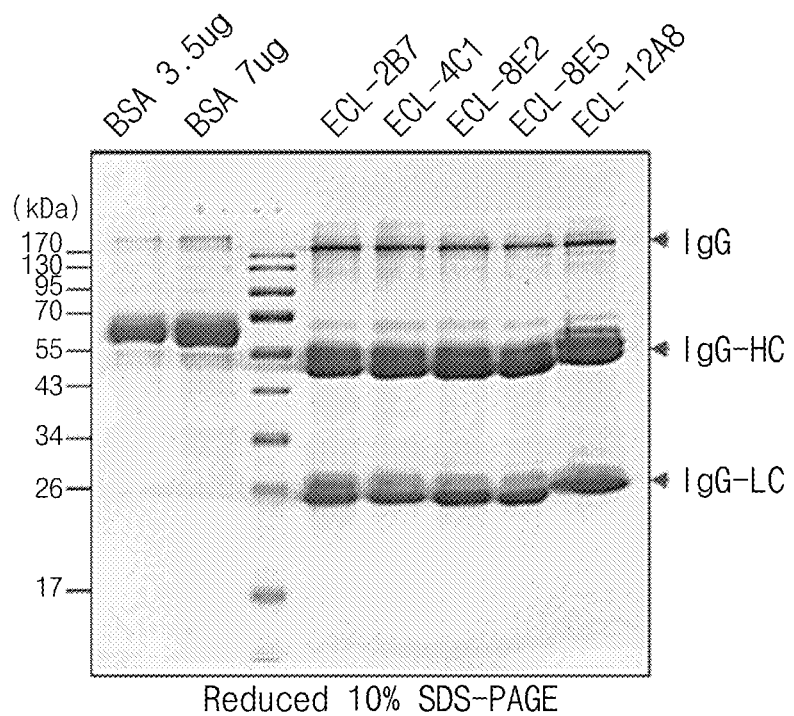
FIG. 2 illustrates a result of confirming the purity by purifying five novel antibodies ECL-2B7, ECL-4C1, ECL-8E2, ECL-8E5 and ECL-12A8 from a hybridoma cell culture solution. From the fact that a heavy chain IgG-HC and a light chain IgG-LC of each antibody are identified at positions of 55 kDa and 26 kDa, respectively, it can be confirmed that the novel antibodies are IgG-type antibodies and unreduced IgG is identified as a band IgG located above 170 kDa, and bovine serum albumin (BSA) is a control for comparing protein amounts.
Figure 4:
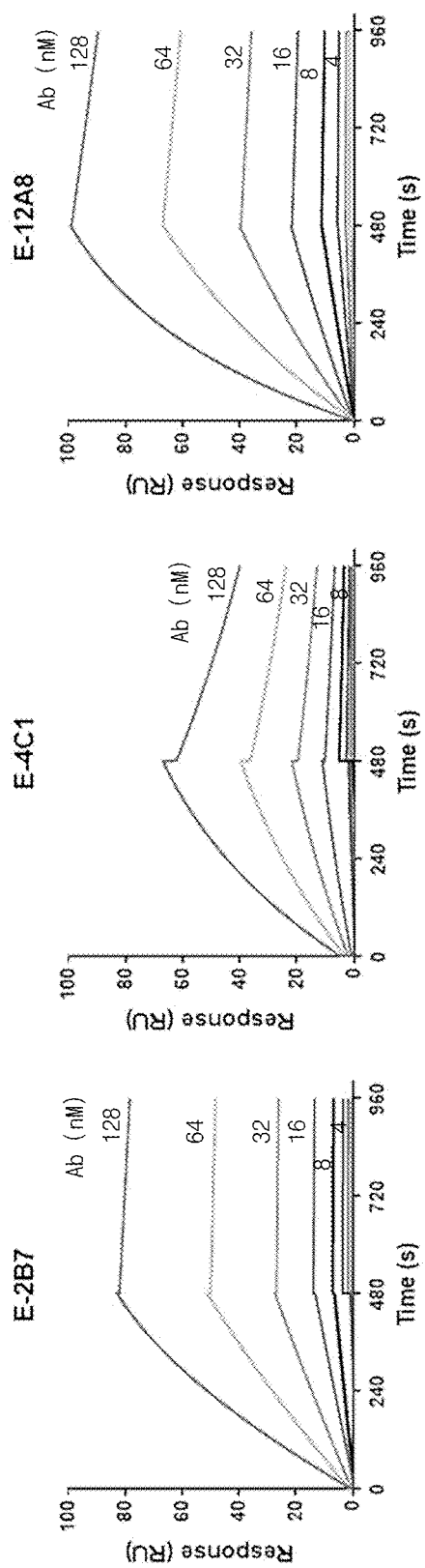
FIG. 4 illustrates a result of confirming the antigen responsivity by the novel antibodies of the present invention by whether the antibody prepared specifically binds to a TM4SF4 protein by using intermolecular interaction analysis (Biocore). Antibodies ECL-2B7, ECL-4C1, and ECL-12A8 were used, and it was observed that a change in specific binding value to each concentration moved significantly, and it was confirmed that a binding value was measured to be high. It can be observed that a binding period in which a graph is increased is increased over time, and when binding is inhibited at 480 seconds, the binding ability is decreased, and this is a typical form of an antibody with high binding ability showed in the intermolecular interaction analysis.

Hereinafter, the present invention will be described in detail.

In an aspect, the present invention provides an antibody or antigen-binding fragment thereof that specifically binds to TransMembrane 4 Superfamily Member 4 (TM4SF4).

In the present invention, the term "antibody" refers to a protein molecule that serves as a receptor for specifically recognizing an antigen, including immunoglobulin molecules that have an immunological responsivity to a specific antigen, and for example, may include all monoclonal antibodies, polyclonal antibodies, full-length antibodies, and antibody fragments. In addition, the term "antibody" may include a bivalent or bispecific molecule (e.g., a bispecific antibody), a diabody, a triabody or a tetrabody.

In the present invention, the term "monoclonal antibody" refers to an antibody molecule of a single molecular composition obtained from substantially the same antibody group, and such a monoclonal antibody exhibits single-binding specificity and affinity against a specific epitope. In the present invention, the term "full-length antibody" is a structure having two full-length light chains and two full-length heavy chains, and each light chain is linked to the heavy chain by a disulfide bond. A heavy chain constant region has gamma (γ), mu (µ), alpha (α), delta (δ), and epsilon (≥) types, and subclasses of gamma1 (γ1), gamma2 (γ2), gamma 3 (γ3), gamma 4 (γ4), alpha 1 (α1) and alpha2 (α2). A light chain variable region has kappa (κ) and lambda (λ) types. IgG is a subtype, and includes IgG1, IgG2, IgG3 and IgG4.

In the present invention, the terms "fragment", "antibody fragment" and "antigen-binding fragment" are used interchangeably as referring to any fragment of the antibody of the present invention that retains an antigen-binding function of the antibody. Exemplary antigen-binding fragments include Fab, Fab', F(ab')$_2$, Fv, dAb, Fd, a complementarity determining region (CDR) fragment, a single-chain antibody (scFv), a bivalent single-chain antibody, a single-chain phage antibody, a diabody, a triabody, a tetrabody, a polypeptide containing one or more fragments of immunoglobulin sufficient to bind to a specific antigen to the polypeptide, and the like, but are not limited thereto.

The Fab has a structure having variable regions of the light and heavy chains, a constant region of the light chain, and a first constant region of the heavy chain (CH1 domain), and has one antigen-binding site. The antigen-binding fragment or antibody fragment of the antibody molecule refers to a fragment that has an antigen-binding function, and Fab' has a hinge region including one or more cysteine residues at a C-terminus of the heavy chain CH1 domain, which is different from Fab. The F(ab')$_2$ antibody is produced when the cysteine residues in the hinge region of Fab' form a disulfide bond. The Fv refers to the smallest antibody fragment having only a heavy chain variable region and a light chain variable region. The double-chain Fv (two-chain Fv) has a heavy chain variable region and a light chain variable region linked by a non-covalent bond, the single-chain Fv may generally form a dimer-like structure such as double-chain Fv because the variable region of the heavy chain and the variable region of the single chain are covalently linked by a peptide linker or directly linked at the C-terminus. Although not limited thereto, these antibody fragments may be obtained using proteolytic enzymes [for example, the entire antibody is restriction-cleaved with papain to obtain Fab, and cleaved with pepsin to obtain an F(ab')₂ fragment], or may be produced through genetic recombination technology.

In the present invention, the term "epitope" refers to a specific site on an antigen to which immunoglobulin, and an antibody or antigen-binding thereof are specifically recognized and bound. The epitope may be formed from continuous amino acids or from discontinuous amino acids paralleled by tertiary folding of the protein.

In one embodiment of the present invention, the present invention provides an antibody or antigen-binding fragment thereof that binds to a TM4SF4 protein in the epitope region in which a membrane protein, TM4SF4 exists in a region exposed outside the cells.

The epitope region may be, for example, GGCARCLGGTLIPLAFFGFLANILLFFPGG (SEQ ID NO: 23) at positions 4 to 33, LGSGVLMIFPALVEL (SEQ ID NO: 24) at positions 53 to 67, NNDCCGCCGN (SEQ ID NO: 25) at positions 71 to 80, STIFAVVGELGAGYSFIISAI (SEQ ID NO: 26) at positions 92 to 112, KGPKCLM (SEQ ID NO: 27) at positions 116 to 122, WGYPFHD (SEQ ID NO: 28) at positions 127 to 133, and CREPLNVVPWNLTLFSILLVVGGIQ MVLCAIQVVNGLLGTLCGDCQCCGCCGG (SEQ ID NO: 29) at positions 146 to 198 from an N-terminus in a reference TM4SF4 antigen (SEQ ID NO: 1). More specifically, the epitope region may be TWGYPFHDGDYLNDE (SEQ ID NO: 2) at positions 126 to 140 from the N-terminus in the reference TM4SF4 antigen (SEQ ID NO: 1).

In addition, even if the epitope region described in SEQ ID NO: 2 includes some mutations (substitution, addition or deletion) in an antigen sequence of TM4SF4 to which the antibody or antigen-binding fragment thereof of the present invention binds, or the binding site or sequence is slightly different as the binding antigen is present in the form of a fragment, a precursor or a subtype of TM4SF4, those skilled in the art may clearly specify a position and a sequence to which the antigen or antigen-binding fragment thereof of the present invention binds, based on epitope sequence information of the reference TM4SF4 antigen.

In a specific embodiment of the present invention, in an antigen structure of TM4SF4, a membrane protein consisting of 202 amino acids, a site which is exposed to the outside of the cell and expected to have high antibody-inducing ability and has no glycosylation or disulfide bonds was selected as an epitope region for producing the antibody (FIG. 1).

As another embodiment of the present invention, the antibody may be (a) an antibody including a heavy chain variable region having CDR-H1 including an amino acid sequence of SEQ ID NO: 3, CDR-H2 including an amino acid sequence of SEQ ID NO: 4, and CDR-H3 including an amino acid sequence of SEQ ID NO: 5; and a light chain variable region having CDR-L1 including an amino acid sequence of SEQ ID NO: 6, CDR-L2 including an amino acid sequence of SEQ ID NO: 7, and CDR-L3 including an amino acid sequence of SEQ ID NO: 8; or (b) an antibody including a heavy chain variable region having CDR-H1 including an amino acid sequence of SEQ ID NO: 9, CDR-H2 including an amino acid sequence of SEQ ID NO: 10, and CDR-H3 including an amino acid sequence of SEQ ID NO: 11; and a light chain variable region having CDR-L1 including an amino acid sequence of SEQ ID NO: 12, CDR-L2 including an amino acid sequence of SEQ ID NO: 13, and CDR-L3 including an amino acid sequence of SEQ ID NO: 14.

In the present invention, the term "heavy chain" may include both a full-length heavy chain and a fragment thereof including a variable region domain VH including an amino acid sequence having a sufficient variable region sequence to impart specificity to the antigen and three constant region domains CH1, CH2 and CH3. In addition, in the present invention, the term "light chain" includes both a full-length light chain and a fragment thereof including a variable region domain VL including an amino acid sequence having a sufficient variable region sequence to impart specificity to the antigen and a constant region domain CL.

In the present invention, the antibody may include all mouse antibodies produced from a mouse and variants obtained by substituting, adding and/or deleting a part of an amino acid sequence of a parent antibody in order to improve the affinity and immunity of the antibody therefrom. The variants are not limited thereto, but examples thereof may include chimeric antibodies, humanized antibodies, affinity optimized antibodies, and the like. The variant generically refers to an antibody in which the same CDR as the parent antibody is included or a part of the parent antibody CDR amino acid sequence is mutated (substituted, added or deleted) under a condition of targeting the same epitope. Such variants may be appropriately adjusted by those skilled in the art in order to improve the affinity and immunity of the antibody within a range in which the binding ability to the same epitope is maintained.

That is, the antibody or antigen-binding fragment thereof of the present invention may include not only a sequence of the anti-TM4SF4 antibody described herein, but also biological equivalents thereof within a range that may specifically recognize TM4SF4. For example, additional changes may be made to the amino acid sequence of the antibody to further improve the binding affinity and/or other biological properties of the antibody. Such modifications include, for example, deletion, insertion and/or substitution of amino acid sequence residues of the antibody. These amino acid variants are made based on the relative similarity of amino acid side-chain substituents, such as hydrophobicity, hydrophilicity, charges, sizes and the like. By analysis of the size, shape and type of the amino acid side-chain substituent, it can be seen that arginine, lysine and histidine are all positively charged residues; alanine, glycine and serine have similar sizes; and phenylalanine, tryptophan and tyrosine have similar shapes. Accordingly, based on these considerations, arginine, lysine and histidine; alanine, glycine and serine; and phenylalanine, tryptophan and tyrosine may be biologically functional equivalents.

In the present invention, the term "chimeric antibody" is an antibody obtained by recombining a variable region of a mouse antibody and a constant region of a human antibody, and an antibody with a greatly improved immune response compared to the mouse antibody.

In the present invention, the term "humanized antibody" refers to an antibody in which a protein sequence of an antibody derived from a non-human species is modified to be similar to an antibody variant naturally produced in the human. For example, the humanized antibody may be prepared by recombining a mouse-derived CDR with a human antibody-derived FR to produce a humanized variable region, and then recombining the produced humanized variable region with a constant region of a preferred human antibody. However, if only CDR grafting is performed, the affinity of the humanized antibody is lowered. Therefore, several important FR amino acid residues that are considered to affect a three-dimensional structure of the CDR are affined with those of the mouse antibody to be increased to the same level as the original affinity of the mouse antibody.

In the present invention, the term "affinity-optimized antibody" refers to a variant in which a part of the CDR sequence of a specific antibody is substituted, added, or deleted, and refers to an antibody with improved binding affinity against the antigen while binding to the same antigen epitope as the specific antibody. Specifically, the affinity-optimized antibody of the present invention refers to a variant antibody that binds to the same epitope as (a) an antibody including a heavy chain variable region having CDR-H1 including an amino acid sequence of SEQ ID NO: 3, CDR-H2 including an amino acid sequence of SEQ ID NO: 4, and CDR-H3 including an amino acid sequence of SEQ ID NO: 5; and a light chain variable region having CDR-L1 including an amino acid sequence of SEQ ID NO: 6, CDR-L2 including an amino acid sequence of SEQ ID NO: 7, and CDR-L3 including an amino acid sequence of SEQ ID NO: 8; or (b) an antibody including a heavy chain variable region having CDR-H1 including an amino acid sequence of SEQ ID NO: 9, CDR-H2 including an amino acid sequence of SEQ ID NO: 10, and CDR-H3 including an amino acid sequence of SEQ ID NO: 11; and a light chain variable region having CDR-L1 including an amino acid sequence of SEQ ID NO: 12, CDR-L2 including an amino acid sequence of SEQ ID NO: 13, and CDR-L3 including an amino acid sequence of SEQ ID NO: 14 of the present invention. Those skilled in the art may prepare the affinity-optimized antibody using known techniques based on specified light and heavy chain CDR sequences.

In another embodiment of the present invention, the antibody may be an antibody having a heavy chain variable region including an amino acid sequence of SEQ ID NO: 15; and a light chain variable region including an amino acid sequence of SEQ ID NO: 16. In one example, the antibody may be an antibody having a heavy chain variable region coded by a nucleotide sequence of SEQ ID NO: 17; and a light chain variable region coded by a nucleotide sequence of SEQ ID NO: 18, but is not limited thereto.

Further, the antibody may be an antibody having a heavy chain variable region including an amino acid sequence of SEQ ID NO: 19; and a light chain variable region including an amino acid sequence of SEQ ID NO: 20. In one example, the antibody may be an antibody having a heavy chain variable region coded by a nucleotide sequence of SEQ ID NO: 21; and a light chain variable region coded by a nucleotide sequence of SEQ ID NO: 22, but is not limited thereto.

In a specific embodiment of the present invention, a hybridoma cell group was obtained from a mouse using a human TM4SF4 protein as an antigen, and from this, screening was performed through an ELISA assay using the TM4SF4 protein as an antigen to select anti-TM4SF4 antibodies that specifically bind to TM4SF4.

In another aspect, the present invention provides a nucleic acid molecule coding the antibody or antigen-binding fragment thereof, an expression vector comprising the nucleic acid molecule, a host cell into which the expression vector is introduced, and a method of producing an antibody or antigen-binding fragment thereof using the host cell.

In the present specification, the term "nucleic acid molecule" has a meaning of comprehensively including DNA and RNA molecules, and nucleotides, which are basic structural units in the nucleic acid molecule, are not only natural nucleotides, but also analogs with modified sugar or base moieties. The sequence of the nucleic acid molecule coding the heavy-chain and light-chain variable regions of the present invention may be modified, and the modification includes addition, deletion, or non-conservative or conservative substitution of the nucleotides.

The nucleic acid molecule of the present invention is interpreted as including a nucleotide sequence exhibiting substantial identity to the nucleotide sequence. In the present invention, the substantial identity means a nucleotide sequence exhibiting homology of at least 80%, specifically homology of at least 90%, and more specifically homology of at least 95%, when aligning the nucleotide sequence of the present invention to correspond to any other sequence as much as possible, and analyzing the aligned sequence using an algorithm commonly used in the art.

In this specification, the term "vector" as a means for expressing a target gene in a host cell includes a plasmid vector; a cozmid vector; and a viral vector such as a bacteriophage vector, an adenovirus vector, a retrovirus vector and an adeno-associated virus vector, and the like, and specifically, may be a plasmid vector, but is not limited thereto.

In the vector of the present invention, the nucleic acid molecule coding the heavy chain variable region and the nucleic acid molecule coding the light chain variable region may be operatively linked with a promoter.

In the present invention, the term "operatively linked" refers to a functional linkage between a nucleic acid expression regulatory sequence (e.g., an array of a promoter, a signal sequence, or a transcriptional regulatory factor binding site) and another nucleic acid sequence, and as a result, the regulatory sequence regulates the transcription and/or translation of the other nucleic acid sequence.

The recombinant vector system of the present invention may be constructed through various methods known in the art.

The vector of the present invention may typically be constructed as a vector for cloning or as a vector for expression. Further, the vector of the present invention may be constructed using prokaryotic or eukaryotic cells as a host.

For example, when the vector of the present invention is an expression vector and a prokaryotic cell is used as a host, the vector generally includes a strong promoter (e.g., tac promoter, lac promoter, lacUV5 promoter, lpp promoter, pLA promoter, pRA promoter, rac5 promoter, amp promoter, recA promoter, SP6 promoter, trp promoter, and T7 promoter, etc.) capable of promoting transcription, a ribosome binding site for initiation of translation, and a transcription/translation termination sequence. When $E.\ coli$ (e.g., HB101, BL21, DH5α, etc.) is used as the host cell, promoter and operator sites of an $E.\ coli$ tryptophan biosynthetic pathway (Yanofsky, C, J Bacteriol, (1984) 158:1018-1024), and a left-facing promoter of phage λ (pLλ promoter, Herskowitz, I and Hagen, D, Ann Rev Genet, (1980) 14:399-445) may be used as a regulatory site. When $Bacillus$ bacteria is used as a host cell, a promoter of a toxin protein gene of $Bacillus\ thuringensis$ (Appl Environ Microbiol (1998) 64:3932-3938; Mol Gen Genet (1996) 250:734-741) or any promoter expressible in *Bacillus* bacteria may also be used as a regulatory site.

On the other hand, the recombinant vector of the present invention may be prepared by manipulating plasmids (e.g., pCL, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19, etc.), phages (e.g. λgt4•λB, λ-Charon, λΔz1 and M13, etc.), or viruses (e.g. SV40, etc.), which have been often used in the art.

On the other hand, when the vector of the present invention is an expression vector and an eukaryotic cell is used as a host, the vector may use promoters (e.g., metallotionine promoter, β-actin promoter, human hemoglobin promoter and human muscle creatine promoter) derived from the genome of mammalian cells or promoters (e.g., adenovirus late promoter, vaccinia virus 75K promoter, SV40 promoter, cytomegalovirus (CMV) promoter, tk promoter of HSV, mouse mammary tumor virus (MMTV) promoter, LTR promoter of HIV, Epstein-barr virus (EBV) promoter of Moloney virus, and Rous sarcoma virus (RSV) promoter) derived from mammalian viruses, and generally has a polyadenylation sequence as a transcription termination sequence. Specifically, the recombinant vector of the present invention includes a CMV promoter.

The recombinant vector of the present invention may be fused with other sequences to facilitate purification of antibodies expressed therefrom. The sequences to be fused include, for example, glutathione S-transferase (Pharmacia, USA), maltose binding protein (NEB, USA), FLAG (IBI, USA), 6× His (hexahistidine; Quiagen, USA), and the like. In addition, since the protein expressed by the vector of the present invention is an antibody, the expressed antibody may be easily purified through a protein A column or the like without an additional sequence for purification.

On the other hand, the recombinant vector of the present invention includes an antibiotic resistance gene commonly used in the art as a selection marker, and may include resistance genes to, for example, ampicillin, gentamicin, carbenicillin, chloramphenicol, streptomycin, kanamycin, geneticin, neomycin and tetracycline.

The vector expressing the antibody of the present invention may be a vector system in which light and heavy chains are simultaneously expressed in one vector, or a system in which light and heavy chains are expressed in separate vectors, respectively. In the latter case, the two vectors may be introduced into a host cell, for example, via co-transformation or targeted transformation. The co-transformation is a method of simultaneously introducing each vector DNA coding a light chain and a heavy chain into a host cell, and then selecting cells expressing both the light chain and the heavy chain. The targeted transformation is a method of selecting cells transformed with a vector containing a light chain (or heavy chain) and transforming the selected cells with a vector containing a heavy chain (or a light chain) again to finally select cells expressing both the light chain and the heavy chain.

Any host cell known in the art capable of stably and continuously cloning and expressing the vector of the present invention may be used as the host cell. For example, the host cell may include *Bacillus* strains such as *Escherichia coli, Bacillus subtilis*, and *Bacillus thuringiensis*, and prokaryotic host cells such as *Streptomyces, Pseudomonas* (e.g., *Pseudomonas putida*), *Proteus mirabilis* or *Staphylococcus* (e.g., *Staphylococcus carnosus*), but is not limited thereto.

Suitable eukaryotic host cells of the vector may use fungi such as *Aspergillus* species, yeasts such as *Pichia pastoris, Saccharomyces cerevisiae, Schizosaccharomyces*, and *Neurospora crassa*, other lower eukaryotic cells, higher eukaryotic cells such as insect-derived cells, and cells derived from plants or mammals.

Specifically, host cells may be COS7 cells (monkey kidney cells), NSO cells, SP2/0, Chinese hamster ovary (CHO) cells, W138, baby hamster kidney (BHK) cells, MDCK, a myeloma cell line, HuT 78 cells or 293 cells, but is not limited thereto.

In the present invention, "transformation" and/or "transfection" into a host cell includes any method of introducing a nucleic acid into an organism, a cell, a tissue or an organ, and may be performed by selecting a suitable standard technique according to a host cell, as known in the art. Such a method includes electroporation, protoplasm fusion, calcium phosphate ($CaPO_4$) precipitation, calcium chloride ($CaCl_2$) precipitation, agitation using silicon carbide fibers, agrobacterial-mediated transformation, PEG, dextran sulfate, lipofectamine and drying/inhibition mediated transformation methods, and the like, but are not limited thereto.

In the present invention, the method of producing the antibody or antigen-binding fragment thereof using the host cell may include the steps of: (a) culturing the host cell transformed with the recombinant vector of the present invention; and (b) expressing an anti-TM4SF4 antibody or antigen-binding fragment thereof in the host cell.

In the antibody production, the transformed host cell may be cultured according to an appropriate medium and culture conditions known in the art. The culturing process may be easily adjusted and used by those skilled in the art according to a selected strain. The cell culture is divided into suspension culture and adhesion culture according to a cell growth method, and batch, fed-batch and continuous culture methods according to a culture method. The medium used for culture needs to adequately meet the requirements of the specific strain.

In the animal cell culture, the medium contains various carbon sources, nitrogen sources, and trace element components. Examples of carbon sources that may be used may include carbohydrates such as glucose, sucrose, lactose, starch fructose, maltose, and cellulose, fats such as soybean oil, sunflower oil, castor oil and coconut oil, fatty acids such as palmitic acid, stearic acid and linoleic acid, alcohols such as glycerol and ethanol, and organic acids such as acetic acid, and these carbon sources may be used alone or in combination.

Examples of nitrogen sources which may be used in the present invention may include organic nitrogen sources, such as peptone, yeast extract, gravy, malt extract, corn sediment liquid (CSL), and soybean meal; and inorganic nitrogen sources such as urea, ammonium sulfate, ammonium chloride, ammonium phosphate, ammonium carbonate, and ammonium nitrate, and these nitrogen sources may be used alone or in combination. In the medium, potassium dihydrogen phosphate, dipotassium hydrogen phosphate, and corresponding sodium-containing salts may be included as a phosphate source. In addition, a metal salt such as magnesium sulfate or iron sulfate may be included. In addition, amino acids, vitamins, suitable precursors, and the like may be included.

During the culture, a compound such as ammonium hydroxide, potassium hydroxide, ammonia, phosphoric acid, and sulfuric acid is added to the culture solution by a proper method to adjust a pH of the culture medium. In addition, during the culture, production of bubbles may be inhibited by using an anti-foaming agent such as fatty acid polyclinic ester. In addition, in order to maintain an aerobic state of the culture solution, oxygen or oxygen-containing gas (e.g., air) is injected into the culture solution. The temperature of the culture solution is usually 20° C. to 45° C., preferably 25° C. to 40° C.

The production method may further include (c) recovering the anti-TM4SF4 antibody or antigen-binding fragment thereof expressed in the host cell. The antibody obtained by culturing the transformed host cell may be used in a non-purified state, or may be further purified and used with high purity using various general methods, such as dialysis, salt precipitation, and chromatography. Among the methods, the method using chromatography is most commonly used, and the type and order of a column may be selected from ion exchange chromatography, size exclusion chromatography, and affinity chromatography depending on the characteristics of an antibody, a culture method, and the like.

In yet another aspect, the present invention provides a composition for detecting TM4SF4 including the antibody or antigen-binding fragment thereof, a detection kit including the same, and a method for detecting a TM4SF4 antigen using the same.

The composition for detecting TM4SF4 and the kit including the same may effectively detect TM4SF4 by contacting the antibody or antigen-binding fragment thereof that specifically binds to TM4SF4 with a sample to be detected to form an antigen-antibody complex.

The term "antigen-antibody complex" as used herein refers to a conjugate of TM4SF4 and an antibody that recognizes the TM4SF4, for confirming tumor or cancer cells expressing TM4SF4 in the sample.

A method for quantifying TM4SF4 antigen using the composition for detecting TM4SF4 and the kit including the same may be performed by confirming the formation of the antigen-antibody complex. The formation of the antigen-antibody complex may be confirmed by enzyme linked immunosorbent assay (ELISA), Western blotting, immunofluorescence, immunohistochemistry staining, flow cytometry, immunocytochemistry, radioimmunoassay (RIA), immunoprecipitation assay, immunodiffusion assay, complement fixation assay, protein chip, or the like, but is not limited thereto. The ELISA includes various ELISA methods, such as direct ELISA using a labeled antibody that recognizes an antigen attached to a solid support, indirect ELISA using a labeled secondary antibody that recognizes a capture antibody in a complex of an antibody that recognizes an antigen attached to a solid support, direct sandwich ELISA using another labeled antibody that recognizes an antigen in a complex of an antibody and an antigen attached to a solid support, indirect sandwich ELISA using a labeled secondary antibody that recognizes an antibody after reacting with another antibody that recognizes the antigen in a complex of the antibody and the antigen attached to a solid support, and the like.

Labels that enable the formation of the antigen-antibody complex to be qualitatively or quantitatively measured include enzymes, fluorescent substances, ligands, luminescent substances, microparticles, redox molecules, and radioisotopes, but are not limited thereto.

The enzyme includes β-glucuronidase, β-D-glucosidase, β-D-galactosidase, urease, peroxidase, alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phospholpyruvate decarboxylase, β-latamase, and the like, but is not limited thereto.

In yet another aspect, the present invention provides a composition for preventing or treating cancer including the antibody or antigen-binding fragment thereof.

The antibody and the antigen-binding fragment thereof are as described above.

Since the antibody or antigen-binding fragment thereof of the present invention binds to TM4SF4 with high affinity to inhibit the growth of cancer cells, the antibody may be used for treating, preventing and diagnosing hyperproliferative diseases such as cancer alone or in combination with a conventional pharmaceutically acceptable carrier.

The cancer that is disease applied to the composition of the present invention may be specifically lung cancer, gastric cancer, colon cancer, rectal cancer, triple breast cancer, glioblastoma, pancreatic cancer, head and neck cancer, breast cancer, ovarian cancer, kidney cancer, bladder cancer, prostate cancer, endometrial cancer, salivary gland cancer or thyroid cancer, and more specifically, lung cancer, breast cancer, liver cancer, kidney cancer, gastric cancer, pancreatic cancer, and brain cancer, but is not limited thereto. In the present invention, the cancer may be particularly cancer caused by overexpression, amplification, mutation or activation of TM4SF4, but is not limited thereto. That is, since the composition including the antibody or antigen-binding fragment thereof of the present invention has a proliferation inhibitory effect on all carcinomas regardless of abnormal expression or mutation 41 TM4SF4, a pharmaceutical use of the present invention is not limited depending on the expression aspect or mutation of TM4SF4.

The composition may be in the form of a pharmaceutical composition, a quasi-drug composition, or a health food composition.

The composition for preventing or treating cancer of the present invention may further include a pharmaceutically acceptable carrier. The 'pharmaceutically acceptable' means that a target to be applied (prescribed) has no toxicity more than adaptable without inhibiting the activity of an active ingredient, and the 'carrier' is defined as a compound that facilitates the addition of a compound into cells or tissues.

The pharmaceutical composition of the present invention may be administered alone or in combination with any convenient carrier and the like, and such dosage forms may be single dosage or repeated dosage forms. The pharmaceutical composition may be a solid formulation or a liquid formulation. The solid formulation includes powders, granules, tablets, capsules, suppositories, and the like, but is not limited thereto. The solid formulation may include a carrier, a flavoring agent, a binder, a preservative, a disintegrant, a lubricant, a filler, etc., but is not limited thereto. The liquid formulation includes solutions such as water and a propylene glycol solution, suspensions, emulsions, and the like, but is not limited thereto and may be prepared by adding suitable coloring agents, flavoring agents, stabilizers, viscous agents, etc. For example, the powders may be prepared by simply mixing a tri-hydroxy derivative of polyunsaturated fatty acid, which is an active ingredient of the present invention, and a suitable pharmaceutically acceptable carrier such as lactose, starch, and microcrystalline cellulose. The granules may be derivative of the prepared by mixing the tri-hydroxy polyunsaturated fatty acid of the present invention, a suitable pharmaceutically acceptable carrier, and a suitable pharmaceutically acceptable binder such as polyvinylpyrrolidone and hydroxypropylcellulose, and then using a wet granulation method using a solvent such as water, ethanol, and isopropanol or a dry granulation method using a compressive force. Further, the tablets may be prepared by mixing the granules with a suitable pharmaceutically acceptable lubricant such as magnesium stearate, and then tableting the mixture using a tablet machine.

The pharmaceutical composition may be administered with an oral agent, an injection (e.g., intramuscular injection, intraperitoneal injection, intravenous injection, infusion, subcutaneous injection, implant), an inhalant, a nasal injection, a vaginal agent, a rectal agent, a sublingual agent, a transdermal agent, a topical agent, or the like according to a disease to be treated and a condition of a subject, but is not limited thereto. Depending on a route of administration, the pharmaceutical composition may be formulated into a suitable dosage unit form including a pharmaceutically acceptable carrier, an additive, and a vehicle, which are commonly used and non-toxic.

The pharmaceutical composition may be administered at a daily dose of about 0.0001 mg/kg to about 10 g/kg, and about 0.001 mg/kg to about 1 g/kg. However, the dosage may vary depending on the degree of purification of the mixture, the patient's condition (age, sex, weight, etc.), the severity of the condition to be treated, and the like. If necessary, for convenience, the total daily dose may be divided and administered several times during a day.

In addition, the present invention provides a composition for inhibiting growth of cancer stem cells, including the antibody or antigen-binding fragment thereof.

In the present invention, the 'cancer stem cell (CSC)' refers to an undifferentiated cell having the ability to differentiate into various cancer cells. The cancer stem cells are present in about 1-2% of malignant tumor tissues, and have self-replicating ability and pluripotency, which are the characteristics of normal stem cells, but have abnormality in the self-regulatory function to increase the number of cells due to activation of cell division and self-differentiate into malignant tumor cells. Due to the characteristics of cancer stem cells, it is known that general cancer cells are removed through anticancer treatment, but cancer stem cells survive, and recurrence and metastasis of cancer are caused by some of the surviving cancer stem cells.

Specifically, the cancer stem cells of the present invention may be cancer cells in which an aldehyde dehydrogenase 1 (ALDH1) protein, which is one of markers of cancer stem cells, is overexpressed or the protein activity is positive.

In the present invention, it was confirmed that the antibody or antigen-binding fragment thereof selectively inhibited the cancer stem cells and, in particular, kills a cancer cell group containing cancer stem cells having high resistance to anti-cancer treatment, thereby obtaining excellent anti-cancer effects. The antibody or antigen-binding fragment thereof of the present invention may inhibit the growth of cancer stem cells by reducing the self-renewal ability, invasion ability, and migration ability of cancer stem cells. The antibody or antigen-binding fragment thereof is not limited thereto, but may be used to prevent or treat cancer having characteristics of cancer stem cells.

Since cancer with the characteristics of cancer stem cells shows resistance to existing anticancer treatments and has a poor prognosis, the cancer needs to be applied with different treatments from existing anticancer treatments. For example, even in patients with the same carcinoma, if the carcinoma corresponds to a case in which the proportion of cancer stem cells is high, the patients will not be able to obtain cancer treatment effects with existing known anti-cancer treatments such as administration of anticancer agents or radiation therapy. Therefore, even with the same type of cancer, it is very important to apply new treatments different from the existing anticancer treatments when the proportion of cancer stem cells is high in cells at a cancer lesion site.

In the present invention, the 'cancer with the characteristics of cancer stem cells' refers to cancer having a high proportion of cancer stem cells in a cell group constituting the cancer. Considering that the proportion of cancer stem cells among general cancer cells is about 1% or more and less than 5%, for example, a case where the proportion of cancer stem cells in a cell group constituting cancer is 5% or more, 10% or more, 30% or more, 50% or more, and 70% or more may be defined as 'the cancer with the characteristics of cancer stem cells', and as described above, it may be characterized that the cancer has a poor anticancer treatment prognosis due to resistance to existing anticancer treatments.

Specifically, in the present invention, the 'cancer with the characteristics of cancer stem cells' may be cancer overexpressing ALDH1. The cancer overexpressing ALDH1 may be cancer which expresses ALDH1 or has a relatively higher proportion of cancer stem cells with the positive activity than general cancer.

Specifically, the 'cancer overexpressing ALDH1' may be at least one selected from the group consisting of lung cancer, breast cancer, liver cancer, kidney cancer, gastric cancer, pancreatic cancer, and brain cancer, but is not limited thereto.

The prevention or treatment of the cancer may be to prevent or treat cancer chemical resistance, cancer recurrence, or cancer metastasis during or after cancer treatment by reducing the renewal ability, growth ability, invasion ability, and migration ability of cancer stem cells.

In still yet another aspect, the present invention provides a composition for adjuvant chemoradiation therapy including the antibody or antigen-binding fragment thereof as an active ingredient.

The composition of the present invention includes the antibody or antigen-binding fragment thereof as an active ingredient for improving radiation sensitivity of cancer-related cells. Details of the antibody and the antigen-binding fragment thereof are as described above.

The cancer-related cells of the present invention are cells constituting cancer, and may have characteristics that the cells are not uniform in shape compared to normal cells, proliferated indefinitely, and have weak binding strength with surrounding cells. Specifically, the cancer-related cells may be cancer cells or cancer stem cells, and specifically, cancer stem cells.

The cancer stem cells may be undifferentiated cells having the ability to differentiate into various cancer cells, and specifically, may be cancer cells expressing ALDH1 or having positive activity. In the present invention, the cancer stem cells may have characteristics such that cell proliferation is not inhibited even by irradiation of radiation, self-renewal ability is not reduced, and migration and invasion abilities are not inhibited.

In addition, the cancer-related cells may have low sensitivity to radiation, that is, have high resistance to radiation therapy, and substantially have no sensitivity to radiation, so that anticancer treatment by irradiation may not be possible.

The anticancer may be inhibiting the proliferation of cancer-related cells, inhibiting metastasis and invasion, and inducing cell death through irradiation, surgical surgery, and chemotherapy. In the present invention, the anticancer may be administered with the antibody or antigen-binding fragment thereof in combination with irradiation. As such, when the antibody or antigen-binding fragment is administered in combination with irradiation, the radiation sensitivity of cancer-related cells is improved by the antibody or antigen-binding fragment, thereby maximizing an anticancer treatment effect by irradiation and further preventing recurrence and metastasis of cancer.

Hereinafter, the present invention will be described in detail by Examples and Experimental Examples.

However, the following Examples and Experimental Examples are just illustrative of the present invention, and the contents of the present invention are not limited to the following Examples and Experimental Examples.

Example 1

Production of Human Monoclonal Antibodies Against TM4SF4-Antigen

<1-1> Selection or Epitope Sequence for Production of Human TM4SF4 Membrane Protein Antigen-Specific Antibody In order to produce a TM4SF4-specific response antibody capable of inhibiting a signaling system related to cancer stem cell characteristics mediated by a TM4SF4 antigen, a site to be exposed to the outside of cells and expected to have high antibody induction ability was to be selected in a structure of a TM4SF4 antigen which was a membrane protein consisting of 202 amino acids.

First, it was confirmed by protein sequencing that the membrane protein, TM4SF4 included two loop structures (amino acid sequences 31 to 45 and 115 to 158) exposed to the outside of the cells. Among them, it was confirmed that asparagines, which were amino acids at positions 124 and 156, were a glycosylation site, and a disulfide bond was formed between cysteines, which were amino acids at positions 120 and 146 (FIG. 1). Next, the TM4SF4 protein sequence was analyzed using an antigenicity prediction program. As a result of analyzing the antigenicity using Kolaskar and Tongaonkar methods for the entire sequence, sequences at positions 4 to 33, 53 to 67, 71 to 80, 92 to 112, 127 to 133, and 146 to 198 were predicted as sites with high antigenicity (Table 1).

<1-2> Selection of Anti-TM4SF4 Antibody-Producing B Cell Hybridoma Clones

A peptide 'CTWGYPFHDGDYLN DE' of a sequence in which cysteine was added to an amino terminus of the selected antigen sequence was synthesized and conjugated to bovine serum albumin (BSA) using Sulfo-SMCC. The prepared antigen was injected three times into 4 mice according to a general immunizing process, and it was confirmed by ELISA whether an antigen-specific response antibody had increased in the blood due to an immunization effect. After the final immunization, splenocytes of mice in which the antibody production was confirmed were collected and fused with mouse myeloma cells to obtain antibody-producing B cell hybridoma cells. A plurality of B cell hybridomas successfully fused using a HAT selection medium was obtained for culturing a fusion cell line, and antigen-specific antibodies were tested in a cell culture solution by ELISA while culturing the cells according to a general protocol of hybridoma cell selection. In the ELISA, an antigen peptide conjugate BSA which had been used for immunization and BSA as a control were used as a coating antigen (100 ng/well).

As a result, five anti-TM4SF4 antibody-producing B cell hybridoma clones ECL-2B7, ECL-4C1, ECL-8E2, ECL-8E5, and ECL-12A8 with a significantly higher response to the TM4SF4 peptide conjugate BSA than the response to the BSA were selected (Table 2).

TABLE 2

| Clone No | OD TM4SF4-ECL |
|---|---|
| 2B7 | 3.654 |
| 4C1 | 3.578 |
| 8E2 | 3.686 |
| 8E5 | 3.521 |
| 12A8 | 3.685 |

TABLE 1

| Start Position | Sequence | End Position | SEQ ID NO |
|---|---|---|---|
| 4 | GGCARCLGGTLIPLAFFGFLANILLFFPGG | 33 | 23 |
| 53 | LGSGVLMIFPALVFL | 67 | 24 |
| 71 | NNDCCGCCGN | 80 | 25 |
| 92 | STIFAVVGFLGAGYSFIISAI | 112 | 26 |
| 116 | KGPKCLM | 122 | 27 |
| 127 | WGYPFHD | 133 | 28 |
| 146 | CREPLNVVPWNLTLFSILLVVGGIQMVLCAIQVVNGLLGTLCGDCQCCGCCGG | 198 | 29 |

In summarizing these results, in the present invention, a site (i.e., 'TWGYPFHDGDYLNDE' consisting of amino acid sequences at positions 126 to 140) having high antigenicity and no glycosylation or disulfide bond as an extracellular exposed site was selected as an antigen epitope for producing an antibody (FIG. 1A).

Antibody-producing cells were identified by performing cell clone selection by limiting dilution over three times, and it was verified by an isotyping kit that antibody globulin subtypes generated by the cells were IgG1, IgG2a, IgG2b, etc., and consisted of a kappa-type light chain (Table 3).

TABLE 3

|        | 2B7   | 4C1   | 8E2   | 8E5   | 12A8  |
|--------|-------|-------|-------|-------|-------|
| IgG1   | 1.688 | 0.213 | 1.995 | 0.130 | 0.063 |
| IgG2a  | 0.049 | 2.652 | 0.067 | 2.511 | 0.053 |
| IgG2b  | 0.054 | 0.072 | 0.151 | 0.154 | 2.357 |
| IgG3   | 0.050 | 0.049 | 0.051 | 0.054 | 0.055 |
| IgA    | 0.045 | 0.050 | 0.048 | 0.051 | 0.051 |
| IgM    | 0.049 | 0.044 | 0.051 | 0.047 | 0.052 |
| Kappa  | 0.556 | 1.286 | 0.532 | 1.133 | 0.895 |
| Lambda | 0.075 | 0.073 | 0.067 | 0.065 | 0.078 |

<1-3> Purification of Novel Antibodies

In order to verify the in vitro/vivo efficacy of novel antibodies, B cell hybridoma clones such as ECL-2B7 were cultured in large quantities, and the antibodies were purified from a culture solution.

Specifically, in order to purify the novel antibodies, each B-cell hybridoma was cultured in a DMEM medium containing 10% bovine serum for 3 to 4 days and prepared to sufficiently produce and then secrete antibodies, and the cell culture solution was collected and used for antibody purification. The collected cell culture solution was treated with ammonium sulfite at a concentration of 50%, centrifuged at 10,000×g for 30 minutes to precipitate the antibodies, and then dissolved in phosphate-buffered saline (PBS, pH 7.4). Since it was confirmed that the isotypes of the antibodies were IgG1, IgG2a, and IgG2b, respectively, the antibodies were purified according to a protocol for using a product using protein G-agarose having high affinity against the antibodies. The purified antibodies were quantified by a Bradford method and an ELISA method, and the purity was confirmed by SDS-PAGE.

As a result, the antibodies were purified with high purity of about 99% by affinity chromatography, and approximately 1 mg per each antibody was obtained in 200 mL of the cell culture solution. A heavy chain (IgG-HC) and a light chain (IgG-LC) of each antibody were identified at positions of 55 kDa and 26 kDa to identify an IgG-type antibody, and the unreduced IgG was identified by a band (IgG) located above 170 kDa.

Example 2

Confirmation of Antigen-Specific Responsivity of Novel Anti-TM4SF4 Antibody

<2-1> Verification of Antigen-Specific Response of Novel Antibodies by Enzyme-Linked Immunosorbent Assay (ELISA)

In order to confirm an antigen-specific responsivity of novel antibodies, a bovine serum albumin antigen (TM4SF4-peptide-BSA) bound with amino acids at positions 126 to 140 which were some peptide sequences was used in an extracellular large loop domain (ECL) of a TM4SF4 protein. Antigen affinity of the novel antibodies was also measured by ELISA using an immunogen, and antibodies with excellent antigen-binding ability were selected.

Specifically, in order to confirm the antibody responsivity to the TM4SF4-peptide-BSA antigen, the antigen was diluted in PBS, dispensed on a 96-well Maxisorp ELISA plate (Nunc), and induced adhesion to prepare a plate coated with the antigen. The antigen was diluted sequentially by 1/5 from starting at a concentration of 500 ng/well, and 100 μl of the diluted antigen was added to individual wells of the plate, and the antigen was induced to be coated on the well surface of the plate for 16 hours or more at 4° C. After antigen coating, the plate was washed twice with 300 μl of a washing solution TBST (TBS containing 0.1% (v/v) tween-20) per well to remove uncoated residual antigens, and a skim milk solution (5% (w/v) skim milk/TBST) as a blocking solution was added by 300 μl and reacted at room temperature for 2 hours to block the remaining portion after antigen coating. The novel anti-TM4SF4 antibody was prepared by sequentially diluting by 1/3 from starting at a concentration of 200 ng/well in the blocking solution, and 100 μl/well of the diluted antibody was added to the blocked plate and then stirred at 37° C. at a speed of 50 rpm for 2 hours to induce antigen/antibody binding. After the reaction, the solution was removed and the plate was washed 5 times with 300 μl/well of a washing solution to remove the antibodies that did not bind to the antigens, and the antibodies bound to the antigens were detected by treating mouse anti-IgG-HRP (Cell signaling technology Co., Ltd.) as a secondary antibody diluted in a ratio of 1:2500 in a blocking buffer. The secondary antibody was also stirred for 90 minutes at 37° C. at a speed of 50 rpm, and then washed 6 times with a washing solution to remove the secondary antibody which was not bound to the anti-TM4SF4 antibody, and then color development reaction was performed using a TMB solution as a substrate for HRP (Thermo Scientific Co., Ltd.), and the antigen-antibody response was quantified by measuring the absorbance at 450 nm.

As a result, it was confirmed that the five anti-TM4SF4 antibodies ECL-2B7, ECL-4C1, ECL-8E2, ECL-8E5, and ECL-12A8 of the present invention prepared in Example 1 all had excellent antigen-binding ability to the peptide antigen. It was confirmed that among them, the antibodies ECL-2B7, ECL-4C1, and ECL-12A8 exhibited particularly higher antigen affinity (FIG. 3).

<2-2> Verification of Intermolecular Interactions of Novel Antibodies by Surface Plasmon Resonance (SPR)

In order to confirm the antigen-specific responsivity of the novel antibodies, TM4SF4-peptide-BSA (Biotin-GSAGGSTWGYPFHDGDYLNDE) used in Example 2-1 was used as an antigen, and antibodies ECL-2B7, ECL-4C1 and ECL-12A8 were treated to measure the antigen-specific response.

Specifically, in order to confirm the antibody responsivity to the TM4SF4-peptide-BSA antigen of each antibody, a surface protein present on a sensor chip was removed using 1M Nacl and 50 mM NaOH reagents. In order to find an optimal immobilization condition of a biotin-peptide (ligand), the concentration of the ligand was attempted to be immobilized to 10 pM to 100 nM. After immobilization, the antibodies ECL-2B7, ECL-4C1, and ECL-12A8 flowed at a concentration of 32 nM to confirm the binding to the antigen, and regeneration was repeated to attempt to stabilize a baseline. After one hour or more, ECL-2B7, ECL-4C1 and ECL-12A8 analytes were analyzed based on the stabilized baseline.

As a result, it was observed that a binding period in which the graph increased was increased over time, and it was confirmed that when the binding was inhibited at 480 seconds, the binding ability was decreased.

Through this, it can be seen that the antibodies ECL-2B7, ECL-4C1, and ECL-12A8 are antibodies with high binding ability to peptide antigens.

<2-3> Verification of Antigen-Specific Response of Novel Antibodies by Western Blotting after Immunoprecipitation In order for novel antibodies showing high responsivity to the TM4SF4 peptide antigen to be used for cell targeting, the responsivity to the tertiary structure of the TM4SF4 antigen expressed in cells needs to be high. In order to verify this, the specific response of the novel antibodies against the TM4SF4 protein antigen expressed in the cells were verified. A flag-epitope-labeled TM4SF4 protein expression vector (pFLAG-TM4SF4) was prepared and expressed in HEK293T cells. Immunoprecipitation was performed on these cell lysates with novel anti-TM4SF4 antibodies, and the FLAG-label was detected after Western blotting to confirm that the antigen immunoprecipitated with the novel antibodies was TM4SF4.

Specifically, the entire gene sequence of the TM4SF4 protein was prepared by PCR reaction using cDNA of A549 cells, human lung cancer cells, as a template DNA and cloned into a p3×FLAG-CMV™-7.1 vector (Sigma-Aldrich) using an EcoRI/BamHI restriction enzyme sequence to construct a vector (3×FLAG-TM4SF4 vector: pFLAG-TM4SF4) in which the TM4SF4 protein was expressed with three FLAG tags at an N-terminus in the cells. Intracellular expression of pFLAG-TM4SF4 was induced into human embryonic kidney cells (Human Embryonic Kidney 293T, HEK293T) by gene transfection. First, $6\times10^5$/well of HEK293T cells were cultured in a DMEM medium containing 5% fetal bovine serum (FBS) for 16 hours in a 100 mm cell culture plate to prepare cells for expressing a 3×FLAG-TM4SF4 protein. The culture solution of the prepared cells were removed, and 36 μg of the 3×FLAG-TM4SF4 vector pFLAG-TM4SF4 and the same amount of polyethyleneimine (PEI, Polysciences Co., Ltd.) were mixed in 1 mL of a DMEM (5% FBS) culture solution and reacted for 15 minutes at room temperature. Then, the mixture was treated in cells containing 9 mL of the culture solution to be subjected to gene transfection. After 15 hours, the cell culture solution was removed, and the cells were cultured again in the DMEM culture solution containing 10% FBS for 48 hours to induce the expression of the 3×FLAG-TM4SF4 protein, and the specific responsivity to the novel antibodies was verified by immunoprecipitation and Western blotting. The gene-transfected cells were dissolved in a RIPA buffer (1% NP40, 0.5% Sodium deoxycholate, 0.1% SDS, phosphatase inhibitors, pretease inhibitors/PBS), sonicated at 21 amplitudes for 5 seconds, and then centrifuge at 13,000 rpm at 4° C. to obtain a cell protein solution. Protein quantification was performed by a Bradford method, 500 μg of a protein was mixed with 5 μg of novel antibodies or a control antibody, mouse anti-GAPDH antibody, at 4° C. for 16 hours to induce antigen/antibody binding of the antibody and the protein, and 30 μl of protein G beads were added and reacted again for 4 hours to bind the antibodies to the beads. In order to remove a non-specific protein, the beads were washed 6 times with the RIPA buffer, and then an SDS sample buffer containing a reducing agent was added and boiled at 95° C., and the protein was developed on a 12% SDS-PAGE gel. The developed protein was transferred to a PVDF membrane, the membrane on which the protein transfer was completed was blocked for 1 hour at room temperature with a TBST (Tris-buffered saline, 0.1% Tween 20) blocking solution containing 5% (w/v) skim milk, and the anti-FLAG antibody (Cell signaling technology) diluted in the blocking solution was treated at room temperature for 2 hours and then stirred and washed 8 times with TBST for 5 minutes to remove the non-specific antibodies. The anti-FLAG antibody bound to the 3×FLAG-TM4SF4 protein was treated with a secondary antibody (rabbit anti-IgG-HRP) and then detected by an enhanced chemiluminescence (ECL) method.

Figure 5:
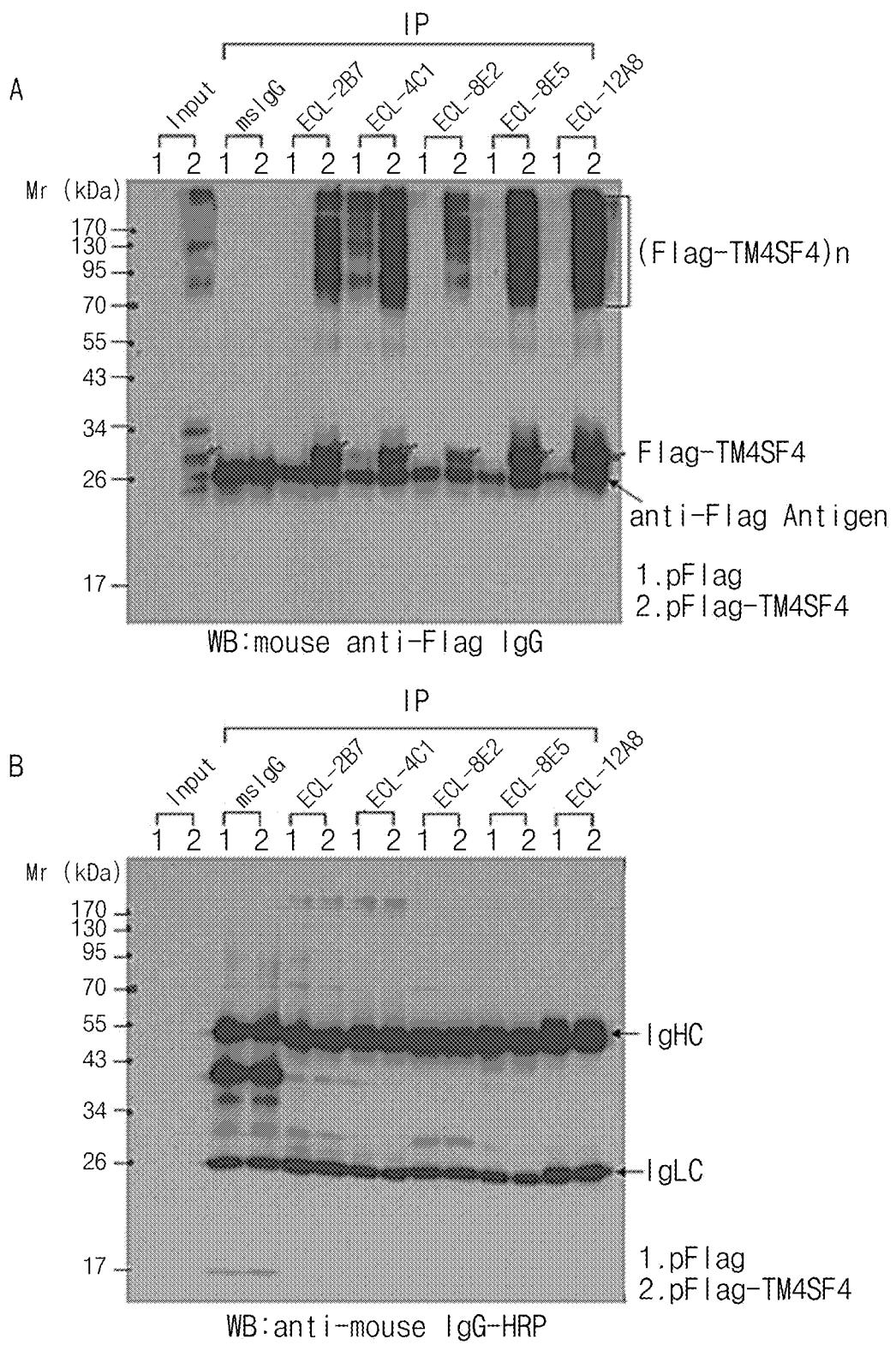
FIG. 5 illustrates results of confirming the antigen responsivity by the novel antibodies of the present invention by whether the antibody prepared specifically binds to the TM4SF4 protein by analysis of immunoprecipitates. A in FIG. 5 illustrates a result of immunoprecipitating cell lysates (Samples 1 and 2) obtained by expressing Flag expression or a Flag-TM4SF4 expression vector in HEK293T cells using a novel antibody or a mouse anti-GAPDH antibody as a control antibody and detecting the immunoprecipitate with an anti-Flag antibody by Western blotting. B in FIG. 5 illustrates a result of verifying an antibody dosage with anti-mouse antibody HRP for the immunoprecipitate to verify whether the same amount of antibody has been added to the immunoprecipitation experiment.

As a result, the predicted molecular weight of the 3×FLAG-TM4SF4 protein was 24.8 kDa, and the anti-FLAG antibody response to the cell lysate expressing the 3×FLAG or 3×FLAG-TM4SF4 protein (input samples of lines 1 and 2 in A in FIG. 5) was confirmed. As a result, the specific response was confirmed at a position of 26 to 30 kDa, and the specific response was also confirmed even at molecular weight positions of 34 kDa and 95 kDa or higher. It has already been confirmed that the TM4SF4 protein had tetraspanin properties that form covalent bonds with surrounding proteins using cysteine residues. It was determined that the reason why the Flag label in the high molecular-weight protein was different from that of the control was that the TM4SF4 protein formed a conjugate by cysteine residues. It was confirmed that the novel antibodies used for immunoprecipitation did not immunoprecipitate the FLAG-labeled protein in a cell lysate (Sample 1) gene-transfected with a control p3×FLAG-CMV™-7.1 vector (pFLAG), while in a cell lysate (Sample 2) gene-transfected with a 3×FLAG-TM4SF4 vector (pFLAG-TM4SF4), 3×FLAG-TM4SF4 was specifically detected by immunoprecipitation at a position of 26 kDa or more. As a result, the specific response of the novel antibodies against TM4SF4 expressed in cells was verified (A in FIG. 5). In addition, in the samples with 26 kDa of 3×FLAG-TM4SF4 confirmed, it was confirmed that proteins with a molecular weight of 95 kDa or higher were also detected by immunoprecipitation, and these samples were proved to be multiple conjugates of the TM4SF4 protein. In the case of a protein band identified below 26 kDa of FLAG-TM4SF4, the proteins were also detected even in a sample treated with a mouse anti-GAPDH antibody (msIgG) used as a negative control immunoprecipitation antibody during immunoprecipitation, and thus, it was determined as the non-specific binding of the anti-FLAG antibody (A in FIG. 5, anti-FLAG Antigen). All the antibodies used during immunoprecipitation were mouse-derived antibodies, and were detected by treating mouse anti-IgG-HRP in a PVDF membrane, and as a result, it was confirmed that the same amount of antibodies was used during immunoprecipitation (B in FIG. 5).

<2-4> Verification of Cell Surface Antigen-Specific Response of Novel Antibodies by Immunofluorescence In order to confirm whether the novel antibodies may specifically recognize cell surface-expressed TM4SF4, the binding ability to the cell surface-expressed TM4SF4 was verified by immunofluorescence analysis.

Specifically, in order to confirm an intracellular expression position of TM4SF4, an N-terminus of TM4SF4 was labeled with a green fluorescent protein, EGFP (Enhanced green fluorescent protein), so that the TM4SF4 exhibits green fluorescence when expressed in cells to prepare a transgenic vector. The entire gene sequence of the TM4SF4 protein was prepared by PCR using cDNA of A549 cells, human lung cancer cells, as a template DNA and cloned into a pEGFP-C2 vector (Clonetech Co., Ltd.) using an EcoRI/BamHI restriction enzyme sequence to construct a vector (EGFP-TM4SF4 vector) in which the TM4SF4 protein was expressed with a EGFP tag at an N-terminus in the cells. Intracellular expression of EGFP-TM4SF4 was induced into human embryonic kidney cells (Human Embryonic Kidney 293T, HEK293T) by gene transfection. First, $1\times10^5$/well of HEK293T cells were cultured in a DMEM medium containing 5% fetal bovine serum (FBS) for 16 hours in a cell culture 6-well plate input with a cover-slide to prepare cells for expressing an EGFP-TM4SF4 protein. The culture solution of the prepared cells was removed, and 6 μg of the EGFP-TM4SF4 vector and the same amount of polyethyl-eneimine (PEI, Polysciences Co., Ltd.) were mixed in 400 μl of a DMEM (5% FBS) culture solution and reacted for 15 minutes at room temperature. Then, the mixture was treated in cells containing 1.6 mL of the culture solution to be subjected to gene transfection. After 15 hours, the cell culture solution was removed, and the cells were cultured again in the DMEM culture solution containing 10% FBS for 48 hours to induce the expression of the EGFP-TM4SF4 protein, and the response between the novel antibodies and the cell-expressing TM4SF4 was confirmed by immunofluorescence analysis. The process of immunofluorescence analysis was as follows. After induction of the expression of the EGFP-TM4SF4 protein, the culture solution of the plate was fully removed, and a culture solution containing 2% paraformaldehyde was pretreated at room temperature for 2 minutes, and then a 2% paraformaldehyde fixative mixed in PBS was stirred at room temperature for 15 minutes to fix the cells (fixation). After the cell fixation process, the cells were washed three times for 5 minutes with a PBS washing solution containing 0.1% bovine serum albumin (BSA) to remove the remaining fixative, and in order to prevent non-specific binding of the antibodies, the cells were blocked with a blocking solution (1% BSA/PBS) for 30 minutes. The novel antibodies were diluted in the blocking solution at a concentration of 50 μg/mL and treated at room temperature for 1 hour to induce antibody-antigen binding, and then washed three times for 5 minutes with a washing solution to remove residual antibodies without binding to the antigen. The antigen-bound antibodies were treated with a mouse anti-IgG-Rhodamine (RDM) secondary antibody diluted in a ratio of 1:1000 in a blocking solution for 1 hour, and the washing solution was treated three times for 5 minutes, and then cell nuclei were stained with a DAPI solution for 5 minutes and confirmed with a confocal laser scanning microscope. The green fluorescence of EGFP was measured to confirm the expression of EGFP-TM4SF4, and the red fluorescence of Rhodamine was measured to confirm antibody response sites.

In addition, when the expression of TM4SF4 was inhibited by treating siRNA in lung cancer cells, A549, overexpressing TM4SF4, it was confirmed that the novel antibody response was reduced. TM4SF4-specific siRNA [sense, 5'-gcc ucu caa ugu ggu ucc cug gaa u-3' (SEQ ID NO: 30); antisense, 5'-auu cca ggg aac cac auu gag agg c-3' (SEQ ID NO: 31)] or a control Stealth RNAi™ Negative Control Medium GC (Invitrogen) was transferred into A549 cells using Lipofectamine® RNAiMAXreagent (Invitrogen) and collected for 48 hours, and then 1×10$^5$ cells were cultured in a dish prepared with a cover glass for 24 hours. After removing the culture solution of the cultured cells, the cells were fixed with a paraformaldehyde solution as described above, and novel antibodies were reacted. The antigen-bound antibodies were treated with a mouse anti-IgG-FITC secondary antibody diluted in a ratio of 1:1000 in a blocking solution for 1 hour, and the washing solution was treated three times for 5 minutes, and then cell nuclei were stained with a DAPI solution for 5 minutes and confirmed with a fluorescence microscope.

Figure 6A:
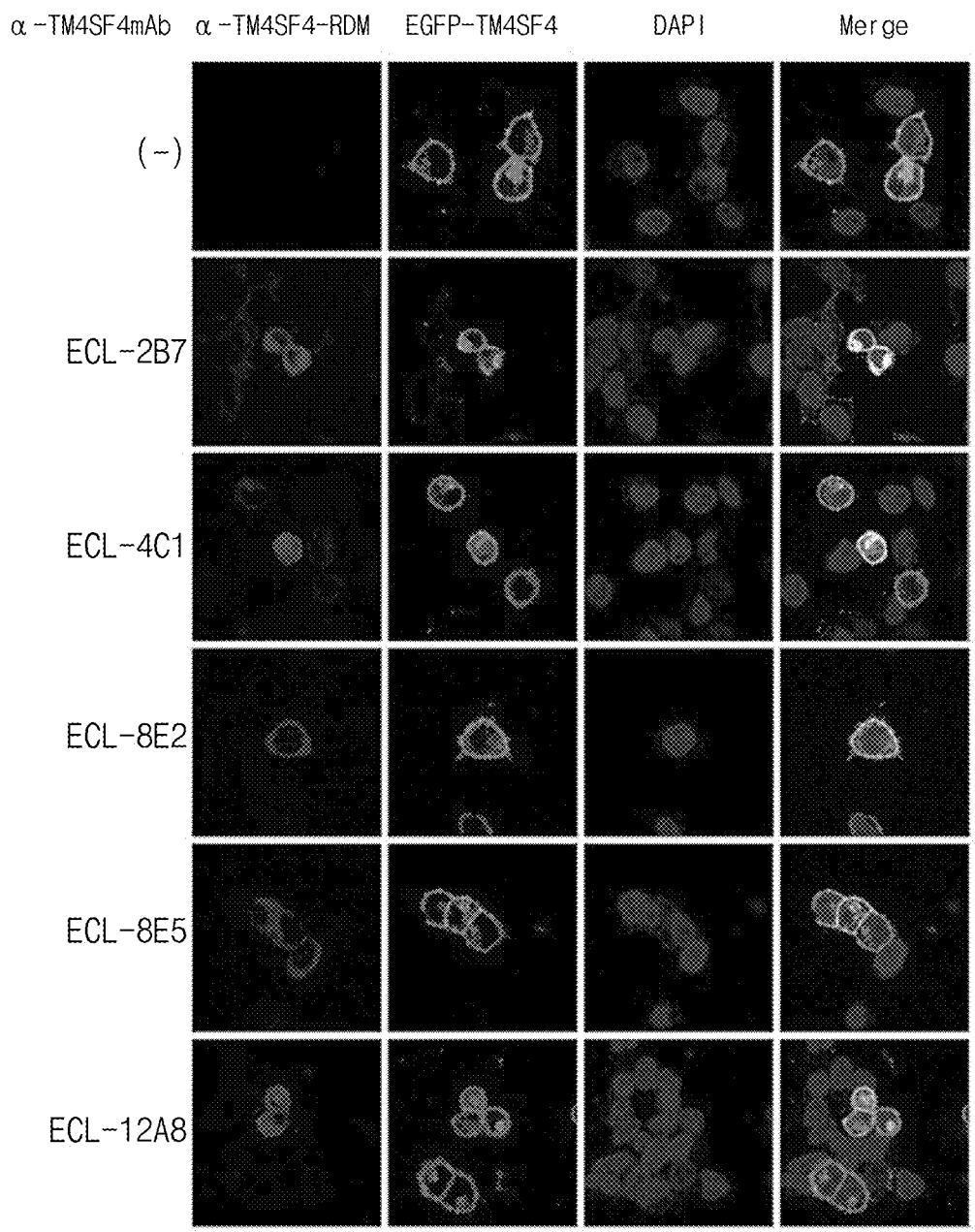
FIG. 6A and FIG. 6B illustrate results of performing immunofluorescence analysis to verify whether the novel antibodies of the present invention specifically bind to a target antigen.

As a result, as illustrated in FIG. 6A, it was confirmed that the EGFP-TM4SF4 protein was located on the cell surface when expressed in HEK293 cells through the expressed green EGFP signal, and novel antibodies-antigen response detected by a red fluorescence signal of Rhodamine was confirmed inside the cells including the cell surface. In addition, when the two signals of red and green were merged, it was confirmed that the two signals existed at the same position, and a yellowish site was located on the cell membrane.

Figure 6B:
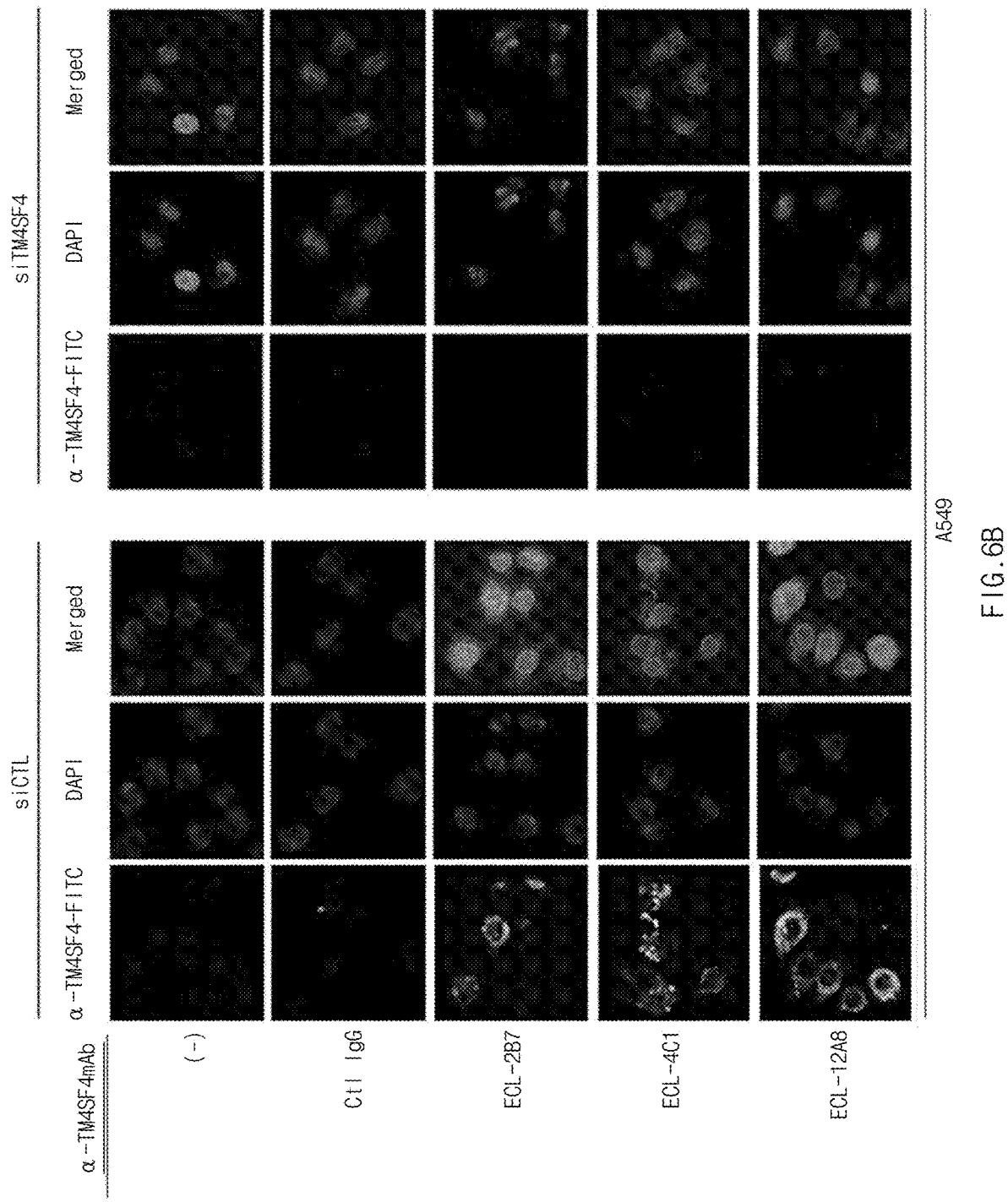

From this, it was verified that all the five novel antibodies were bound to the TM4SF4 protein located on the cell surface, and it was confirmed that the responsivity of ECL-2B7, ECL-4C1, and ECL-12A8 among them was higher. A549 cells were cells with high TM4SF4 expression, and it was confirmed that the cell surface response of the novel antibodies ECL-2B7, ECL-4C1, and ECL-12A8 was high (FIG. 6B). However, when the expression of TM4SF4 was inhibited by treating si-TM4SF4, the antibody response could not be confirmed, thereby confirming the antigen-specific response of the novel antibodies once again.

Example 3

Confirmation of Growth Inhibitory Effect of Cancer Stem Cells by Anti-TM4SF4 Antibody Sphere forming assay, and invasion and migration assays were performed to confirm an effect of inhibiting cancer stem cell characteristics of the novel antibodies with confirmed TM4SF4 antigen response specificity.

<3-1> Isolation and Culture of Cancer Stem Cells

Specifically, human lung cancer cell line, A549 cells were cultured in a humidified 5% $CO_2$ condition at 37° C. The cells were cultured in RPMI supplemented with 10% fetal bovine serum and streptomycin (100 g/ml). Among the cells, A549-ALDH1+ cancer stem cells were isolated and used in subsequent experiments.

<3-2> Confirmation of Effect of Inhibiting Self-Renewal Ability of Cancer Stem Cells by Novel Antibodies A549-ALDH1$^+$ cancer stem cells were cultured in a cancer stem cell acceptable containing a DMEM-F12 (Invitrogen), an medium epidermal growth factor (EGF: 20 ng/ML), a basic fibroblast growth factor (20 ng/mL) and a 2% B27 serum-free supplement (1:50). As a cell incubator, an ultra-low attachment 96-well plate (Corning Co., Ltd.) was used. After 1 to 2 cells per well of the incubator were added and stabilizing for 24 hours, novel antibodies or anti-TM4SF4 antibodies from Sigma Co., Ltd. were treated in the cell culture solution at a concentration of 3 μg/ml, respectively. After treatment, the cells were cultured in a humidified 5% $CO_2$ cell incubator at 37° C., and after 10 days, the number and sizes of spheres formed for cancer stem cells were confirmed using a microscope.

Figure 7:
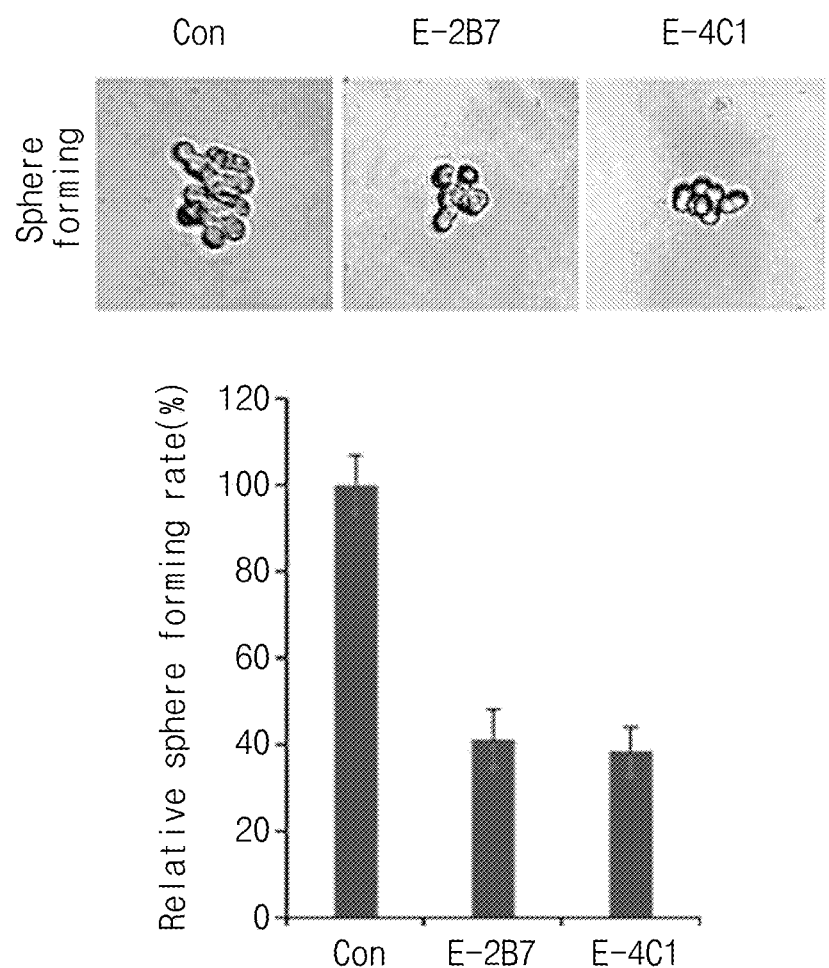
FIG. 7 illustrates confirming an effect of inhibiting the self-renewal ability of cancer stem cells by the novel antibodies of the present invention. ECL-2B7 and ECL-4C1 were used as the novel antibodies, and an anti-TM4SF4 antibody of Sigma was used as a control (con). The left side is to observe the sphere-forming ability of cancer stem cells with an optical microscope, and the right side is a graph showing a diameter length of the formed spheres.

As a result, as illustrated in FIG. 7, it was confirmed that when the novel antibodies of the present invention were treated, the number and sizes of spheres formed were significantly reduced compared to the case of treatment with known antibodies.

From the above results, it can be seen that the ability to form spheres of cancer stem cells may be effectively inhibited through the inhibition of TM4SF4 present in the cell membrane of cancer stem cells, and as a result, it can be seen that the self-renewal ability of cancer stem cells is inhibited.

<3-3> Confirmation of Effect of Inhibiting Invasion and Migration Abilities of Cancer Cells by Novel Antibodies A549 cells (5×10$^4$ cells/well) were suspended in 0.2 ml of a serum-free RPMI medium. For the invasion analysis, cells were dispensed into an upper well of a transwell chamber with an 8-μm pore size pre-coated with 10 mg/ml of Matrigel. The prepared upper well was put on a lower well chamber filled with 0.8 ml of a serum-containing RPMI medium and cultured at 37° C. for 48 hours, and then invasive cells moved to the outside of the upper filter were stained and analyzed. In the movement analysis, a chamber in which Matrigel was not coated on an insert used in the invasion experiment was used. The antibodies were added in the upper well while the cells were dispensed at a concentration of 3 μg/mL.

As a result, as illustrated in FIG. 8, it was confirmed that when the novel antibodies of the present invention were treated, the number of cancer stem cells in which migration and invasion occurred was significantly reduced compared to the case of treating known antibodies.

From this, it can be seen that the novel antibodies of the present invention can effectively inhibit the invasion and migration abilities of cancer cells.

Example 4

Confirmation of Effect of Inhibiting Resistance to Radiation of Cancer Cells by Anti-TM4SF4 Antibody A549 cells and Huh7 cells were coated at $1 \times 10^3$ cells/dish on a 35 mm dish, respectively. After 24 hours, the cell culture solution was treated with novel antibodies ECL-2B7, ECL-4C1, and ECL-12A8 or anti-TM4SF4 antibody from Sigma Co., Ltd. at a concentration of 3 µg/ml, respectively. After treatment, the cells were cultured in a humidified 5% $CO_2$ cell incubator at 37° C. for 7 days. The plate from which the culture solution was removed was stained with a 0.5% crystal violet reagent for 10 minutes, washed several times with PBS, and confirmed under a microscope. In order to confirm the irradiation sensitivity, A549 cells were irradiated with a total radiation dose of 6 Gy (dose rate: x/hour) using a 60Co γ-ray source and coated on a plate, and then treated with antibodies after 24 hours.

Figure 9:
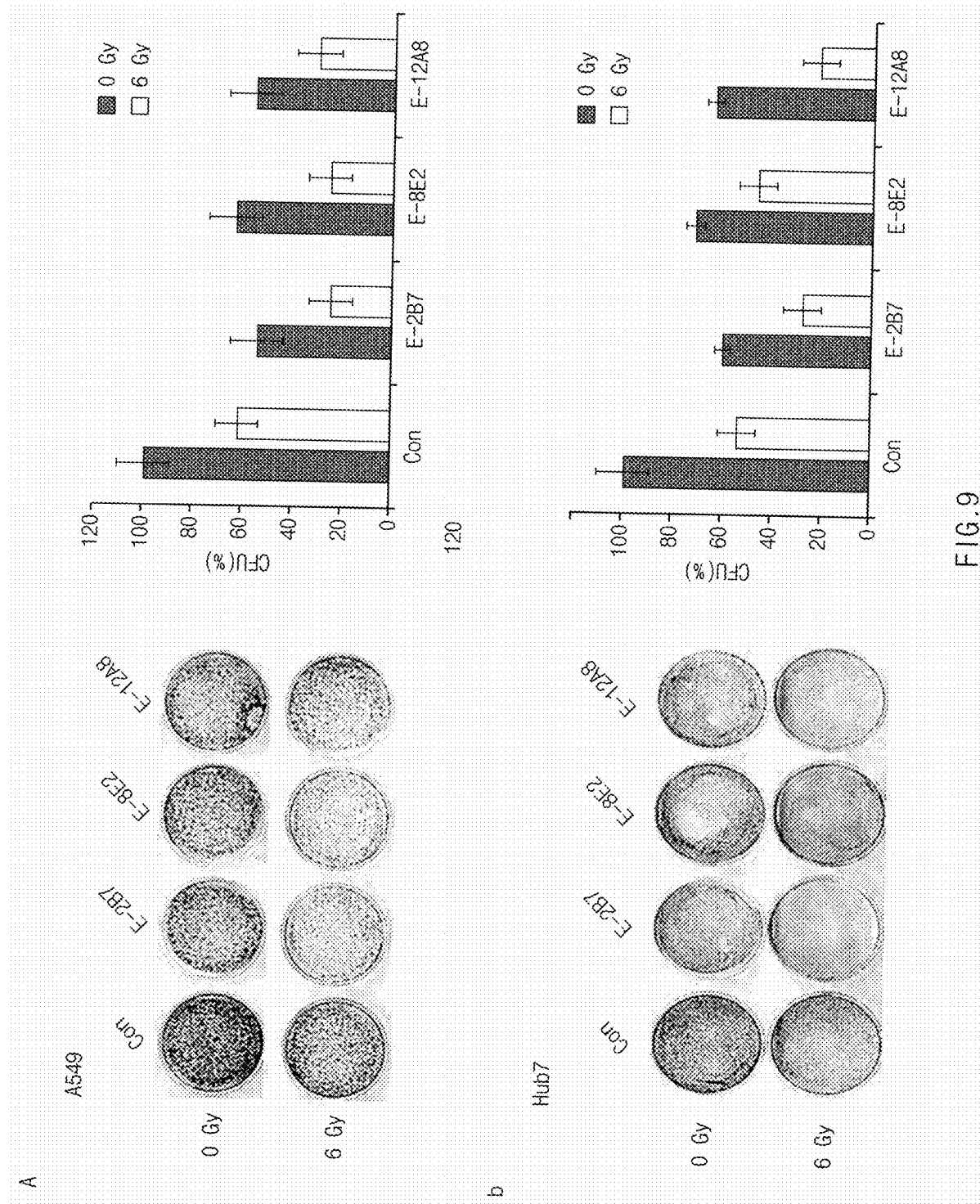
FIG. 9 illustrates confirming an effect of improving the radiation sensitivity of cancer cells by the novel antibodies of the present invention. A549 cells (A) and Huh7 cells (B) were treated with antibodies ECL-2B7, ECL-4C1, and ECL-12A8 and then irradiated with 6 Gy of radiation to confirm that the colony formation of cells was reduced.

As a result, as illustrated in FIG. 9, it was confirmed that colonies of cells survived when treated with the novel antibodies of the present invention were significantly smaller than colonies of cells survived when treated with known antibodies. In addition, it was confirmed that similar effects were shown in not only lung cancer cells but also liver cancer cells.

From this, it can be seen that the novel antibodies of the present invention may be used as a method of increasing a radiation treatment effect, and may be used as a method of increasing the radiation treatment effect in not only lung cancer cells but also liver cancer cells.

Example 5

Confirmation of Intracellular Signaling Process Associated with Induction of Cancer Cell Death by Anti-TM4SF4 Antibody In order to verify the intracellular signaling process involved in the induction of cancer cell death of the novel antibodies of the present invention, the TM4SF4-related signaling process was confirmed and whether the TM4SF4-related signaling process was affected by the antibodies was examined.

Specifically, as confirmed in the previous study results, the expression of proteins was confirmed by Western blotting with respect to whether the expression of IGF1, IL1beta, and Osteopontin, which were products of the signaling process increased by TM4SF4 expression, was inhibited by treatment with the novel antibodies. For the Western blot experiment, each cell was collected, 50 µl of a protein lysis solution was added at a time, reacted at 4° C. for 30 minutes, and then a pellet and a supernatant were separated with a 4° C. centrifuge at 13000 RPM. The supernatant was loaded onto an SDS-PAGE gel by 40 µg of each protein using a protein assay kit (Sigma). Thereafter, the protein loaded on the SDS-PAGE gel was transferred to a nitrocellulose membrane and reacted with a BSA buffer at room temperature for 30 minutes to prevent other antibodies from binding, reacted for 4 hours in a PBS buffer in which primary antibodies TM4SF4, ALDH1A1, ALDH1A3 (Abcam), β-catenin, CD133, Oct4 (millipore), and CD44 and β-actin (cell signaling) were diluted at 1:1000, and then reacted again for 1 hour in a PBS buffer in which a secondary antibody anti-Rabbit or anti-Mouse Igs-HRP (cell signaling) was diluted at 1:10000. Thereafter, the nitrocellulose membrane was washed 5 times with PBS, and then reacted with an ECL detection solution, and then exposed to a film.

Figure 10:
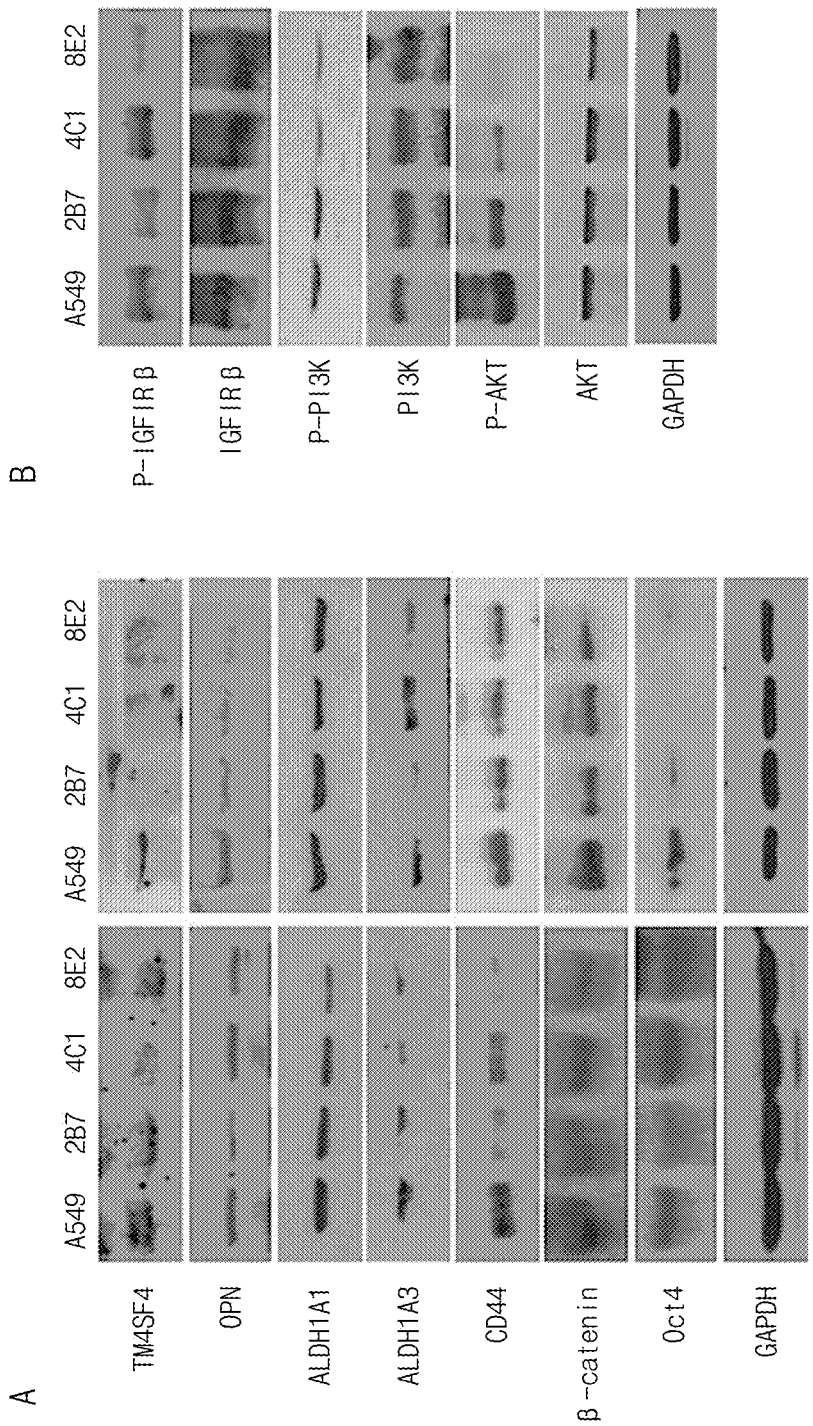
FIG. 10 illustrates confirming mechanisms of the novel antibodies by Western blotting. ECL-2B7, ECL-4C1, ECL-8E2, and ECL-12A8 were used as the antibodies, and A549 cells were used as the cancer cells. When each antibody was treated, it was observed that ALDH1A1, ALDH1A3, and CD44 as labeled proteins of cancer stem cells were decreased, and β-catenin and Oct4 involved in the self-renewal of cancer stem cells were decreased. In addition, it was confirmed that IGF1B and PI3K-AKT signaling pathways known as signaling pathways involved in markers and self-renewal ability regulators were reduced when each antibody was treated, so that the novel antibodies of the present invention inhibited the IFG1Rβ and PI3K-AKT signaling pathways to regulate the cancer stem cells.

As a result, as illustrated in FIG. 10, it was observed that after antibody treatment, labeled proteins ALDH1A1, ALDH1A3, and CD44 of cancer stem cells were reduced when treated with an anti-TM4SF4 antibody, and the expression of β-catenin and Oct4 involved in self-renewal of cancer stem cells was also decreased. In addition, it was observed that among signaling mechanisms involved in cancer malignization, an IGF1Rβ signaling mechanism was involved. It was found that the malignization of cancer stem cells was regulated through the IGF1Rβ signal. From this, it can be seen that the tumor inhibitory effect and the radiation sensitivity improving effect by the novel antibodies of the present invention are effects by killing cancer stem cells, inhibiting self-renewal ability, and inhibiting invasion and migration abilities.

Example 6

Mouse Xenograft Assay for Confirming Cancer Cell Killing Effect of Novel Antibodies In order to confirm the cancer cell killing efficacy of the novel antibodies under an in vivo condition, a lung cancer cell xenograft was formed in a mouse, and novel antibodies were injected to verify growth inhibition/or death of cancer cells.

Specifically, a mouse used to form the lung cancer xenograft was Balb/c nude, and at 6-week age, $1 \times 10^6$ cells/mouse of A549 cells were injected subcutaneously in the right hind limb. After the injection, when the size of the cancer tissue grew to a size of 100 mm³, the TM4SF4 antibody was directly injected into the cancer tissue, and the size of the cancer tissue was measured at intervals of 2 to 3 days. The injected antibody was injected with total 80 µg per mouse, divided 6 times into 13.333 µg/mouse per injection at intervals of 2 to 3 days. The entire experiment was performed until day 49 after injection of cancer cells. The cancer tissue size was calculated by calculation of short axis²×(long axis/2) using a diameter of the cancer tissue.

Two experiments were conducted by varying the timing of antibody administration according to a cancer tissue size. In a first experiment, after 4 weeks of the injection of cancer cells, the antibodies started to be administered when the size of the cancer tissue was 30 mm³ or more.

Figure 11:
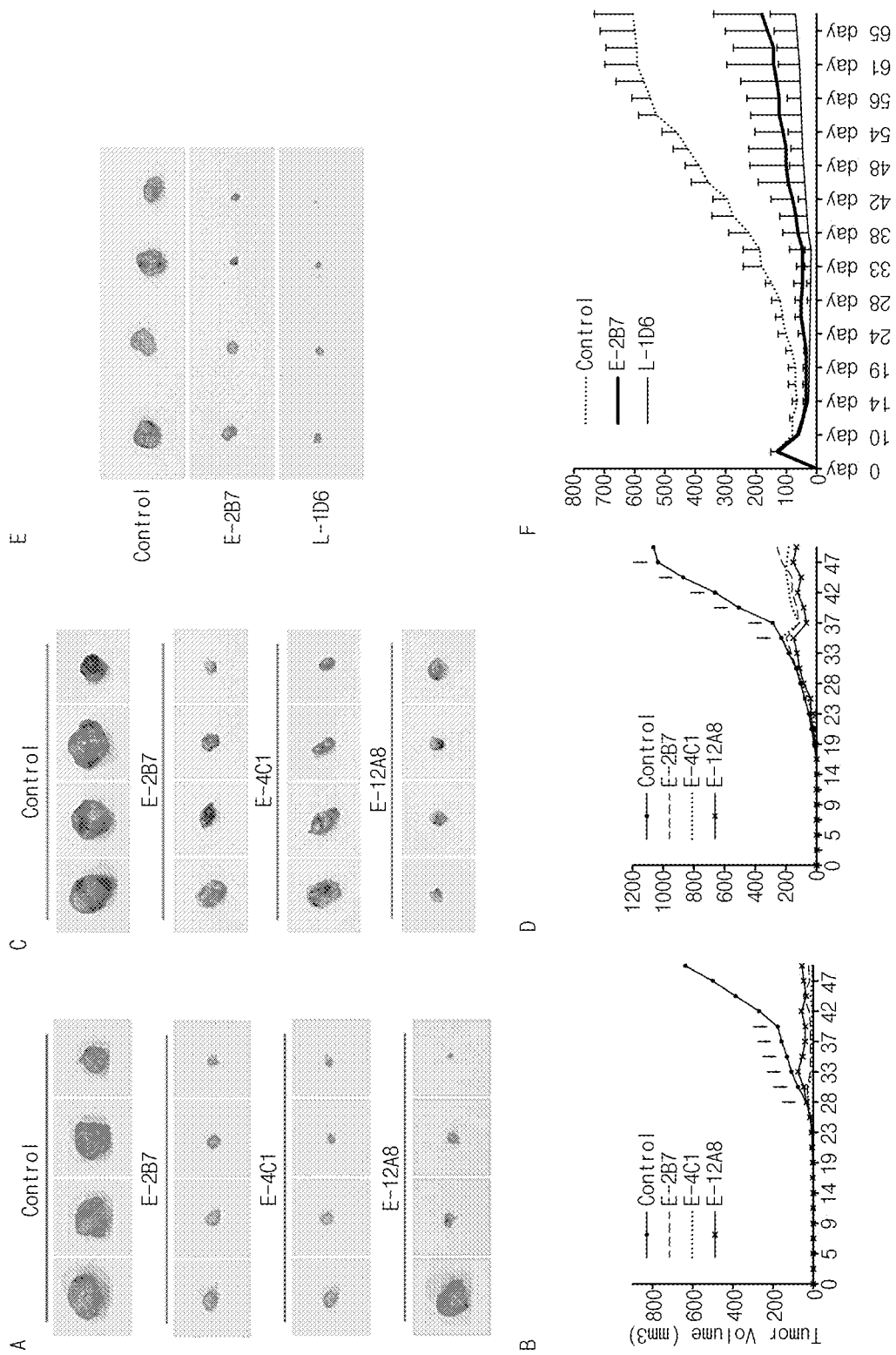
FIG. 11 illustrates results of performing a lung cancer Xenograft assay animal experiment to verify an anticancer effect of the novel antibodies of the present invention. When the sizes of the cancer tissue were 30 mm$^3$ or more (A, B) or 200 mm$^3$ or more (C, D), the antibodies were directly injected into the cancer tissue. In the two experiments, the antibodies were injected at a level of to 13 µg per subject at a time in the same manner for a total of 6 times (arrow dates in B and D), and the sizes of cancer tissues were measured at intervals of 2 to 3 days.

As a result, the growth of the cancer tissue in a group administered with the antibody was inhibited, and the size of the cancer tissue did not increase any more (FIGS. 11A and 11B). In a second experiment, after 5 weeks of the injection of cancer cells, the antibodies started to be administered when the size of the cancer tissue was 200 mm³ or more. At this time, it was also observed that the growth of cancer cells was inhibited in the antibody-injected group. However, it was confirmed that the cancer cell size was maintained and the cancer size slightly increased after the antibody injection was stopped, and as a result, it was determined that there was a correlation between the tumor size and the amount of antibody capable of maximizing the effect when the antibody was used as an anticancer agent (FIGS. 11C and 11D).

In a third experiment, an anti-TM4SF4 antibody was injected into blood vessels instead of direct injection into a cancer to observe a change in the size of the cancer tissue. As a result, results similar to those of the experiments described above could be obtained (FIGS. 11E and 11F).

Example 7

Cloning and Nucleotide Sequencing of Antibody Genes of Novel Monoclonal Antibodies ECL-2B7 and ECL-4C1

The antibody specificity was to be found by determining a complementarity binding region (CDR) to the antigen of the novel antibody. To determine a protein sequence corresponding to the CDR region of the novel antibody, the antibody gene was cloned and the nucleotide sequence of the CDR region was determined.

Specifically, $5\times10^6$ of vigorous hybridomas ECL-2B7 or ECL-4C1 cell clones were collected by centrifugation, and total RNA was extracted with an RNAiso plus reagent (TaKaRa, Otsu, Japan) according to a protocol of a provider. The obtained total RNA was quantified by measuring an OD260 value. The total RNA was added to a PrimeScript RT Master (TaKaRa) Mix to prepare a reverse transcriptase chain reaction mixture and synthesize cDNA.

In order to clone the antibody gene, known PCR primers were modified and used (Wang, et al 2000, J. Immunol. Methods 233:167). For heavy chain cloning with synthesized CDNA, a PCR mixture was prepared by adding 10 pmole of oligonucleotide which was a nucleotide sequence of 5'-GGA GTC GAC ATA GAC AGA TGG GGG TGT CGT TTT GGC-3' (SEQ ID NO: 32) (IgG1 subtype constant region) or 5'-GGA GTC GAC CTT GAC CAG GCA TCC TAG AGT CA-3' (SEQ ID NO: 33) (IgG2a subtype constant region) as a PCR primer corresponding to a constant region of each of an IgG1 subtype antibody ECL-2B7 and an IgG2a subtype antibody ECL-4C1 and oligonucleotide which was a nucleotide sequence of 5'MH1 5'-ctt ccg gaa ttc SAR GIN MAG CTG SAG SAG TC-3' (SEQ ID NO: 34) and 5'MH2-5'-ctt ccg gaa ttc SAR GIN MAG CTG SAG SAG TCW GG-3' (SEQ ID NO: 35) as a primer corresponding to an N-terminus of a heavy chain antibody variable region. For light chain cloning, oligonucleotide of 5'-ggt gtc gac GGA TAC AGT TGG TGC AGC ATC-3' (SEQ ID NO: 36) as a primer corresponding to a kappa chain constant region and 5'MK 5'-cgg aag ctt GAY ATT GTG MTS ACM CAR WCT MCA-3' (SEQ ID NO: 37) as a primer corresponding to an N-terminus of a kappa chain variable region were used, respectively. For efficient cloning of the PCR products, a SalI restriction enzyme site was given to a 3'-primer terminus in the case of a light chain, and a HindIII restriction enzyme site was given in the case of a 5'-primer. In the case of a heavy chain, EcoRI was given to the 5'-primer, and a SalI restriction enzyme site was given to a 3'-primer. After heavy-chain and light-chain reaction solutions were mixed, respectively, the reaction was performed 30 times at 95° C. for 1 minute, 40° C. for 1 minute, and 72° C. for 1 minute. In order to clone the amplified ECL-2B7 and ECL-4C1 genes, the PCR product was first treated with EcoRI and SalI for the heavy chain, and HindIII and SalI for the light chain, and then developed on a 1.0% (w/v) agarose gel. Then, DNA corresponding to about 400 bp and 390 bp was isolated with a FavorPrep GEL™ PCR Purification Kit (Favorgen Co., Ltd., Taiwan). PBluescript KS+ to be used as a vector for cloning a heavy chain gene was treated with EcoRI and SalI, and pBluescript KS+ was treated with HindIII and SalI as a light chain gene cloning vector, and then isolated with a FavorPrep GEL™ PCR Purification Kit (FIGS. 12C and 12D). These two DNAs were linked with T4 DNA ligase (New England Biolab, USA), and transformed into E. coli DH50 by a $CaCl_2$) method. Clones having a DNA insert of a size of about 400 bp in the case of the heavy chain, and E. coli clones having a size of about 390 bp in the case of the light chain were selected.

For DNA sequencing analysis of antibody genes, the several clones were cultured overnight in 3 ml of an LB medium containing 100 μg/ml ampicillin, and then plasmid DNA was isolated using a DNA-Spin plasmid mini prep kit (Intron, Korea), and a nucleotide sequence of each DNA insert was confirmed through nucleotide sequencing (Bionics, Korea).

As a result, as a result of gene amplification of the monoclonal antibodies ECL-2B7 and ECL-4C1, the amplified DNAs may be obtained at a position corresponding to about 400 bp which was a length to be estimated as a DNA fragment corresponding to the heavy chain constant region and a position corresponding to about 390 bp which was a length to be estimated as a DNA fragment corresponding to the light chain constant region (FIGS. 12A and 12B). After cloning the DNAs, the results of analyzing the nucleotide sequences of the DNA inserts (FIGS. 12C and 12D) were obtained, nucleotide sequences of heavy-chain and light-chain DNAs were translated into amino acids, and then CDRs 1, 2, and 3 were indicated in the sequence by arranging an antigen recognition determining site according to an antibody structure through Kabat numbering. As a result of antibody sequence comparison analysis, the heavy chains of the antibodies ECL-2B7 and ECL-4C1 belonged to a subgroup IIIC, and the light chains thereof belonged to a subgroup V (FIGS. 13 and 14).

Example 8

Verification of Extendibility to Other Carcinomas Through Comparison of Colony Formation Ability In order to confirm the degree of inhibiting malignization of various cancer cells by novel antibodies, a comparison experiment of colony formation ability of cells was conducted.

Specifically, for a colony forming assay, lung cancer cells H1299, liver cancer cells Huh7, breast cancer cells MCF7 and MDA-MB 231, and pancreatic cancer cells MIA-Paca-2 were coated at $1\times10^3$ cells/dish on a 35 mm dish. After 24 hours, a novel antibody ECL-2B7 was treated in a cell culture solution at a concentration of 5 μg/ml, respectively. After treatment, the cells were cultured in a humidified 5% $CO_2$ cell incubator at 37° C. for 7 days. The plate from which the culture solution was removed was stained with a 0.5% crystal violet reagent for 10 minutes, washed several times with PBS, and confirmed under a microscope.

Figure 15:
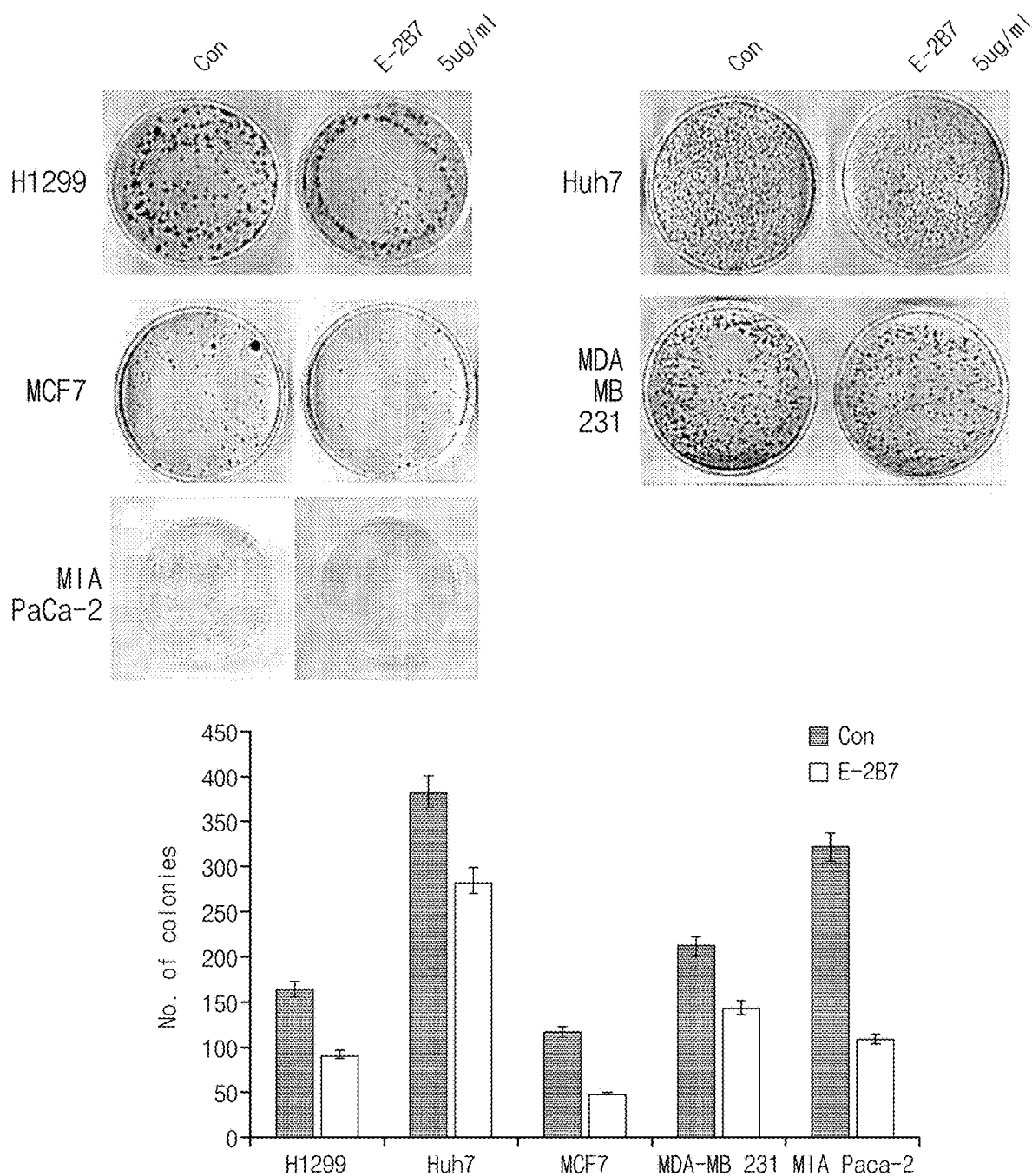
FIG. 15 illustrates results of observing an effect of killing cancer cells by the novel antibodies of the present invention through the colony formation ability. A lung cancer cell line (H1299), a liver cancer cell line (Huh7), a breast cancer cell line (MCF7 and MDA-MB 231) and a pancreatic cancer cell line (MIA Paca-2) were used, and an ECL-2B7 anti-TM4SF4 antibody (experimental group) and mouse IgG (control) were treated in each cell by 5 µg, respectively, and then the colony formation ability of the cells was confirmed. It can be observed that the degree of colony formation is decreased in all the cell lines used, which shows that the antibodies of the present invention may be applied on not only lung cancer cells, but also liver cancer cells, breast cancer cells, and pancreatic cancer cells.

As a result, it was confirmed that even in not only lung cancer cells, but also liver cancer cells and breast cancer cells, the degree of colony formation decreased when the novel antibodies of the present invention were treated (FIG. 15).

Through this, it can be seen that an anticancer treatment technology for various cancers can be proposed by using TM4SF4 antigen-specific binding of novel antibodies.

The invention claimed is:

1. An antibody or antigen-binding fragment thereof that specifically binds to TransMembrane 4 Superfamily Member 4 (TM4SF4), wherein
the antibody binds to an epitope region including an amino acid sequence of SEQ ID NO: 2, wherein the antibody is
(a) an antibody including a heavy chain variable region having CDR-H1 including the amino acid sequence of SEQ ID NO: 3, CDR-H2 including the amino acid sequence of SEQ ID NO: 4, and CDR-H3 including the amino acid sequence of SEQ ID NO: 5; and a light chain variable region having CDR-L1 including the amino acid sequence of SEQ ID NO: 6, CDR-L2 including the amino acid sequence of SEQ ID NO: 7, and CDR-L3 including the amino acid sequence of SEQ ID NO: 8; or
(b) an antibody including a heavy chain variable region having CDR-H1 including the amino acid sequence of SEQ ID NO: 9, CDR-H2 including the amino acid sequence of SEQ ID NO: 10, and CDR-H3 including the amino acid sequence of SEQ ID NO: 11; and a light chain variable region having CDR-L1 including the amino acid sequence of SEQ ID NO: 12, CDR-L2 including the amino acid sequence of SEQ ID NO: 13, and CDR-L3 including the amino acid sequence of SEQ ID NO: 14.

2. The antibody or antigen-binding fragment thereof of claim 1, wherein the antibody includes a heavy chain variable region including the amino acid sequence of SEQ ID NO: 15; and a light chain variable region including the amino acid sequence of SEQ ID NO: 16.

3. The antibody or antigen-binding fragment thereof of claim 1, wherein the antibody includes a heavy chain variable region including the amino acid sequence of SEQ ID NO: 19; and a light chain variable region including the amino acid sequence of SEQ ID NO: 20.

4. The antibody or antigen-binding fragment thereof of claim 1, wherein
the antigen-binding fragment is Fab, F(ab'), F(ab')$_2$ or Fv.

5. A nucleic acid molecule coding the antibody or antigen-binding fragment thereof of claim 1.

6. An expression vector comprising the nucleic acid molecule of claim 5.

7. A host cell comprising the expression vector of claim 6.

8. A method for producing an antibody or antigen-binding fragment thereof comprising culturing the host cell of claim 7.

9. A composition for detecting TM4SF4 comprising the antibody or antigen-binding fragment thereof of claim 1.

10. A kit for detecting a TM4SF4 in a biological sample comprising the antibody or antigen-binding fragment thereof of claim 1.

11. A method for detecting a TM4SF4 antigen comprising contacting the antibody or antigen-binding fragment thereof of claim 1 with a sample to be detected which is expected to include the TM4SF4 antigen.

12. A method for treating a TM4SF4$^+$cancer in a subject in need thereof comprising administering to the subject a composition comprising a therapeutically effective dose of the antibody or antigen-binding fragment thereof of claim 1; and a pharmaceutically acceptable carrier.

13. The method for treating a TM4SF4$^+$cancer of claim 12, wherein the treatment of cancer is to treat cancer chemical resistance, cancer recurrence, or cancer metastasis during or after cancer treatment.

14. The method for treating a TM4SF4$^+$cancer of claim 12, wherein the TM4SF4$^+$cancer is at least one selected from the group consisting of lung cancer, gastric cancer, Ovarian cancer, cervical cancer, breast cancer, pancreatic cancer, colon cancer, rectal cancer, esophageal cancer, skin cancer, thyroid cancer, kidney cancer, liver cancer, head and neck cancer, bladder cancer, prostate cancer, blood cancer, multiple myeloma, acute myelogenous leukemia, malignant lymphoma, thymus cancer, osteosarcoma, fibrotic tumor and brain cancer.

15. A method for inhibiting growth of TM4SF4$^+$cancer stem cells comprising contacting the antibody or antigen-binding fragment thereof of claim 1 with the TM4SF4$^+$ cancer stem cells.

16. A method for improving chemoradiation therapy of TM4SF4$^+$cancer cells comprising contacting the antibody or antigen-binding fragment thereof of claim 1 with the TM4SF4$^+$cancer cells.

17. The method for improving chemoradiation therapy of TM4SF4$^+$cancer cells of claim 16, wherein the antibody or antigen-binding fragment thereof enhances the sensitivity to radiation of the TM4SF4$^+$ cancer cells including TM4SF4$^+$ cancer stem cells.

* * * * *

SEQUENCE LISTING

<160> NUMBER OF SEQ ID NOS: 31

<210> SEQ ID NO 1
<211> LENGTH: 202
<212> TYPE: PRT
<213> ORGANISM: Artificial Sequence
<220> FEATURE:
<223> OTHER INFORMATION: Synthesized

<400> SEQUENCE: 1

Met Cys Thr Gly Gly Cys Ala Arg Cys Leu Gly Gly Thr Leu Ile Pro
1               5                   10                  15

Leu Ala Phe Phe Gly Phe Leu Ala Asn Ile Leu Leu Phe Phe Pro Gly
            20                  25                  30

Gly Lys Val Ile Asp Asp Asn Asp His Leu Ser Gln Glu Ile Trp Phe
        35                  40                  45

Phe Gly Gly Ile Leu Gly Ser Gly Val Leu Met Ile Phe Pro Ala Leu
    50                  55                  60

Val Phe Leu Gly Leu Lys Asn Asn Asp Cys Cys Gly Cys Cys Gly Asn
65                  70                  75                  80

Glu Gly Cys Gly Lys Arg Phe Ala Met Phe Thr Ser Thr Ile Phe Ala
                85                  90                  95

Val Val Gly Phe Leu Gly Ala Gly Tyr Ser Phe Ile Ile Ser Ala Ile
            100                 105                 110

Ser Ile Asn Lys Gly Pro Lys Cys Leu Met Ala Asn Ser Thr Trp Gly
        115                 120                 125

Tyr Pro Phe His Asp Gly Asp Tyr Leu Asn Asp Glu Ala Leu Trp Asn
    130                 135                 140

Lys Cys Arg Glu Pro Leu Asn Val Val Pro Trp Asn Leu Thr Leu Phe
145                 150                 155                 160

Ser Ile Leu Leu Val Val Gly Ile Gln Met Val Leu Cys Ala Ile
            165                 170                 175

Gln Val Val Asn Gly Leu Leu Gly Thr Leu Cys Gly Asp Cys Gln Cys
            180                 185                 190

Cys Gly Cys Cys Gly Gly Asp Gly Pro Val
        195                 200

<210> SEQ ID NO 2
<211> LENGTH: 15
<212> TYPE: PRT
<213> ORGANISM: Artificial Sequence
<220> FEATURE:
<223> OTHER INFORMATION: Synthesized

<400> SEQUENCE: 2

Thr Trp Gly Tyr Pro Phe His Asp Gly Asp Tyr Leu Asn Asp Glu
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Synthesized

<400> SEQUENCE: 3

Thr Tyr Gly Ile Gly Val Ser
1               5

<210> SEQ ID NO 4

```
<211> LENGTH: 16
<212> TYPE: PRT
<213> ORGANISM: Artificial Sequence
<220> FEATURE:
<223> OTHER INFORMATION: Synthesized

<400> SEQUENCE: 4

His Ile Trp Trp Asn Asp Asn Lys Tyr Tyr Asn Thr Ala Leu Lys Ser
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Synthesized

<400> SEQUENCE: 5

Lys Glu Gly Ser Ser Ala Pro Phe Ala Tyr
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthesized

<400> SEQUENCE: 6

Lys Ser Ser Gln Ser Leu Leu Asn Ser Ser Asn Gln Lys Asn Tyr Leu
1               5                   10                  15

Ala

<210> SEQ ID NO 7
<211> LENGTH: 7
<212> TYPE: PRT
<213> ORGANISM: Artificial Sequence
<220> FEATURE:
<223> OTHER INFORMATION: Synthesized

<400> SEQUENCE: 7

Phe Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Gln Gln His Tyr Arg Thr Pro Pro Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthesized

<400> SEQUENCE: 9

Thr Tyr Gly Leu Gly Val Gly
1               5
```

```
<210> SEQ ID NO 10
<211> LENGTH: 16
<212> TYPE: PRT
<213> ORGANISM: Artificial Sequence
<220> FEATURE:
<223> OTHER INFORMATION: Synthesized

<400> SEQUENCE: 10

His Ile Trp Trp Asn Asp Asn Lys Tyr Tyr Asn Thr Ala Leu Lys Ser
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Synthesized

<400> SEQUENCE: 11

Lys Glu Gly Thr Ser Ala Pro Phe Ala Phe
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthesized

<400> SEQUENCE: 12

Lys Ser Ser Gln Ser Leu Leu Asn Gly Ser Asn Gln Lys Gln Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthesized

<400> SEQUENCE: 13

Phe Ala Ser Thr Arg Glu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

Gln Gln His Tyr Arg Thr Pro Pro Thr
1               5

<210> SEQ ID NO 15
<211> LENGTH: 120
<212> TYPE: PRT
<213> ORGANISM: Artificial Sequence
<220> FEATURE:
<223> OTHER INFORMATION: Synthesized

<400> SEQUENCE: 15

Glu Val Lys Leu Glu Glu Ser Gly Pro Gly Ile Leu Gln Pro Ser Gln
1               5                   10                  15
```

```
Thr Leu Ser Leu Thr Cys Ser Phe Ser Gly Phe Ser Leu Ser Thr Tyr
            20                  25                  30

Gly Ile Gly Val Ser Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
 50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Lys Glu Gly Ser Ser Ala Pro Phe Ala Tyr Trp Gly Gln
            100                 105                 110

Gly Thr Leu Val Thr Val Ser Ala
            115                 120

<210> SEQ ID NO 16
<211> LENGTH: 114
<212> TYPE: PRT
<213> ORGANISM: Artificial Sequence
<220> FEATURE:
<223> OTHER INFORMATION: Synthesized

<400> SEQUENCE: 16

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
 50                  55                  60

Pro Asp Arg Phe Ile Gly Ser Gly Ser Gly Thr Asp Phe Thr Leu Thr
65                  70                  75                  80

Ile Ser Ser Met Gln Ala Glu Asp Leu Ala Asp Tyr Phe Cys Gln Gln
                85                  90                  95

His Tyr Arg Thr Pro Pro Thr Phe Gly Gly Gly Thr Lys Leu Glu Ile
            100                 105                 110

Lys Arg

<210> SEQ ID NO 17
<211> LENGTH: 360
<212> TYPE: DNA
<213> ORGANISM: Artificial Sequence
<220> FEATURE:
<223> OTHER INFORMATION: Synthesized

<400> SEQUENCE: 17
gaggtgaagc tggaggagtc tggccctggg atattgcagc cctcccagac cctcagtctg      60
acttgttctt tctctgggtt ttcactgagc acttatggta taggagtaag ctggattcgt     120
cagccttctg ggaagggtct ggagtggctg gcacacattt ggtggaatga taataagtac     180
tataacacag ccctgaagag ccggctcaca atctccaagg atacctccaa caaccaggta     240
ttcctcaaga tcgccagtgt ggacactgca gatactgcca catactactg tgctcgaaag     300
gagggcagct cggccccctt tgcttactgg ggccaaggga ctctggtcac tgtctctgca     360

<210> SEQ ID NO 18
<211> LENGTH: 342
```

```
<212> TYPE: DNA
<213> ORGANISM: Artificial Sequence
<220> FEATURE:
<223> OTHER INFORMATION: Synthesized

<400> SEQUENCE: 18
gatattgtga tgacccagtc tccatcctcc ctggctatgt cagtaggaca gaaggtcact      60
atgagctgca agtccagtca gagccttta  aatagtagca atcaaaagaa ctatttggcc    120
tggtaccagc agaaaccagg acagtctcct aaacttctga tatactttgc atccactagg    180
gaatctgggg tccctgatcg cttcataggc agtggatctg ggacagattt cactcttacc    240
atcagcagta tgcaggctga agacctggca gattacttct gtcagcaaca ttatagaact    300
cctccgacgt tcggtggagg caccaagctg gaaatcaaac gg                       342

<210> SEQ ID NO 19
<211> LENGTH: 120
<212> TYPE: PRT
<213> ORGANISM: Artificial Sequence
<220> FEATURE:
<223> OTHER INFORMATION: Synthesized

<400> SEQUENCE: 19

Glu Val Lys Leu Glu Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Leu Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ala Asp Thr Ala Thr
65                  70                  75                  80

Tyr Tyr Cys Ala Ala Ser Val Asp Thr Ala Asp Thr Ala Thr Tyr Tyr
                85                  90                  95

Cys Ala Arg Lys Glu Gly Thr Ser Ala Pro Phe Ala Phe Trp Gly Gln
            100                 105                 110

Gly Thr Leu Val Thr Val Ser Ala
        115                 120

<210> SEQ ID NO 20
<211> LENGTH: 114
<212> TYPE: PRT
<213> ORGANISM: Artificial Sequence
<220> FEATURE:
<223> OTHER INFORMATION: Synthesized

<400> SEQUENCE: 20

Asp Ile Val Met Thr Gln Ser Pro Ser Ser Leu Ala Met Ser Val Gly
1               5                   10                  15

Glu Arg Val Thr Met Ser Cys Lys Ser Ser Gln Ser Leu Leu Asn Gly
            20                  25                  30

Ser Asn Gln Lys Gln Tyr Leu Ala Trp Phe Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
```

```
                        85                   90                  95
His Tyr Arg Thr Pro Pro Thr Phe Gly Gly Thr Lys Leu Glu Ile
                   100                 105                 110

Lys Arg

<210> SEQ ID NO 21
<211> LENGTH: 360
<212> TYPE: DNA
<213> ORGANISM: Artificial Sequence
<220> FEATURE:
<223> OTHER INFORMATION: Synthesized

<400> SEQUENCE: 21
gaagttaagc tggaggagtc tggccctggg atattgcagc cctcccagac cctcagtctg    60
acttgttctt tctctgggtt ttcactgacc acttatggtt taggagtagg ctggattcgt   120
cagccttcag ggaagggtct ggagtggctg gcacacattt ggtggaatga taataagtat   180
tataacacag ccctgaagag ccggctcaca atctccaagg atacctccaa caatcaggta   240
ttcctcaaga tcgccagtgt ggacactgca gatactgcca catactactg tgctcgaaag   300
gagggcacct cggccccctt tgctttctgg ggccaaggga ctctggtcac tgtctctgca   360

<210> SEQ ID NO 22
<211> LENGTH: 341
<212> TYPE: DNA
<213> ORGANISM: Artificial Sequence
<220> FEATURE:
<223> OTHER INFORMATION: Synthesized

<400> SEQUENCE: 22
gatattgtga tgacccagtc tccatcctcc ctggctatgt cagtcggaca gagggtcact    60
atgagctgca agtccagtca gagcctttta aatggtagca tcaaaagaa ctatttggcc   120 tggttccagc agaaaccagg acagtctcct aaacttctgg tatactttgc atccactagg   180
gaatctgggg tccctgatcg cttcataggc agtggatctg ggacagattt cactcttacc   240
atcagcagtg tgcaggctga agacctggca gattacttct gtcagcaaca ttataggact   300
cctccgacgt tcggtggagg caccaagctg gaaataaacg g                       341

<210> SEQ ID NO 23
<211> LENGTH: 30
<212> TYPE: PRT
<213> ORGANISM: Artificial Sequence
<220> FEATURE:
<223> OTHER INFORMATION: Synthesized

<400> SEQUENCE: 23

Gly Gly Cys Ala Arg Cys Leu Gly Gly Thr Leu Ile Pro Leu Ala Phe
1               5                  10                  15

Phe Gly Phe Leu Ala Asn Ile Leu Leu Phe Phe Pro Gly Gly
            20                  25                  30

<210> SEQ ID NO 24
<211> LENGTH: 15
<212> TYPE: PRT
<213> ORGANISM: Artificial Sequence
<220> FEATURE:
<223> OTHER INFORMATION: Synthesized

<400> SEQUENCE: 24

Leu Gly Ser Gly Val Leu Met Ile Phe Pro Ala Leu Val Phe Leu
1               5                  10                  15
```

```
<210> SEQ ID NO 25
<211> LENGTH: 10
<212> TYPE: PRT
<213> ORGANISM: Artificial Sequence
<220> FEATURE:
<223> OTHER INFORMATION: Synthesized

<400> SEQUENCE: 25

Asn Asn Asp Cys Cys Gly Cys Cys Gly Asn
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Synthesized

<400> SEQUENCE: 26

Ser Thr Ile Phe Ala Val Val Gly Phe Leu Gly Ala Gly Tyr Ser Phe
1               5                   10                  15

Ile Ile Ser Ala Ile
            20

<210> SEQ ID NO 27
<211> LENGTH: 7
<212> TYPE: PRT
<213> ORGANISM: Artificial Sequence
<220> FEATURE:
<223> OTHER INFORMATION: Synthesized

<400> SEQUENCE: 27

Trp Gly Tyr Pro Phe His Asp
1               5

<210> SEQ ID NO 28
<211> LENGTH: 7
<212> TYPE: PRT
<213> ORGANISM: Artificial Sequence
<220> FEATURE:
<223> OTHER INFORMATION: Synthesized

<400> SEQUENCE: 28

Lys Gly Pro Lys Cys Leu Met
1               5

<210> SEQ ID NO 29
<211> LENGTH: 53
<212> TYPE: PRT
<213> ORGANISM: Artificial Sequence
<220> FEATURE:
<223> OTHER INFORMATION: Synthesized

<400> SEQUENCE: 29

Cys Arg Glu Pro Leu Asn Val Val Pro Trp Asn Leu Thr Leu Phe Ser
1               5                   10                  15

Ile Leu Leu Val Val Gly Gly Ile Gln Met Val Leu Cys Ala Ile Gln
            20                  25                  30

Val Val Asn Gly Leu Leu Gly Thr Leu Cys Gly Asp Cys Gln Cys Cys
                35                  40                  45

Gly Cys Cys Gly Gly
    50
```

```
<210> SEQ ID NO 30
<211> LENGTH: 25
<212> TYPE: RNA
<213> ORGANISM: Artificial Sequence
<220> FEATURE:
<223> OTHER INFORMATION: Synthesized

<400> SEQUENCE: 30
gccucucaau gugguucccu ggaau                                              25

<210> SEQ ID NO 31
<211> LENGTH: 25
<212> TYPE: RNA
<213> ORGANISM: Artificial Sequence
<220> FEATURE:
<223> OTHER INFORMATION: Synthesized

<400> SEQUENCE: 31
auuccaggga accacauuga gaggc                                              25
```